(12) United States Patent
Zickerman

(10) Patent No.: US 11,406,574 B1
(45) Date of Patent: *Aug. 9, 2022

(54) FACIAL SUNSCREEN COMPOSITION

(71) Applicant: Love Sun Body LLC, West Orange, NJ (US)

(72) Inventor: Terry Zickerman, West Orange, NJ (US)

(73) Assignee: LOVE SUN BODY IP HOLDINGS LLC, West Orange, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/071,995

(22) Filed: Oct. 15, 2020

Related U.S. Application Data

(60) Provisional application No. 62/915,196, filed on Oct. 15, 2019.

(51) Int. Cl.
| | | |
|---|---|---|
| *A61K 8/27* | (2006.01) |
| *A61K 8/34* | (2006.01) |
| *A61K 8/36* | (2006.01) |
| *A61K 8/362* | (2006.01) |
| *A61K 8/365* | (2006.01) |
| *A61K 8/73* | (2006.01) |
| *A61K 8/92* | (2006.01) |
| *A61K 8/02* | (2006.01) |
| *A61Q 17/04* | (2006.01) |
| *A61K 8/29* | (2006.01) |

(52) U.S. Cl.
CPC ............. *A61K 8/27* (2013.01); *A61K 8/0208* (2013.01); *A61K 8/29* (2013.01); *A61K 8/345* (2013.01); *A61K 8/361* (2013.01); *A61K 8/362* (2013.01); *A61K 8/365* (2013.01); *A61K 8/731* (2013.01); *A61K 8/922* (2013.01); *A61Q 17/04* (2013.01); *A61K 2800/412* (2013.01); *A61K 2800/43* (2013.01); *A61K 2800/48* (2013.01); *A61K 2800/522* (2013.01); *A61K 2800/524* (2013.01); *A61K 2800/72* (2013.01); *A61K 2800/87* (2013.01)

(58) Field of Classification Search
None
See application file for complete search history.

(56) References Cited

U.S. PATENT DOCUMENTS

2015/0147362 A1* 5/2015 Drovetskaya ........ A61K 8/4966
424/401

* cited by examiner

*Primary Examiner* — Nannette Holloman
(74) *Attorney, Agent, or Firm* — Vivacqua Crane, PLLC

(57) ABSTRACT

The present disclosure relates to non-comedogenic and hypoallergenic sunscreen compositions that comply with COSMOS-standard AISBL.

20 Claims, 18 Drawing Sheets

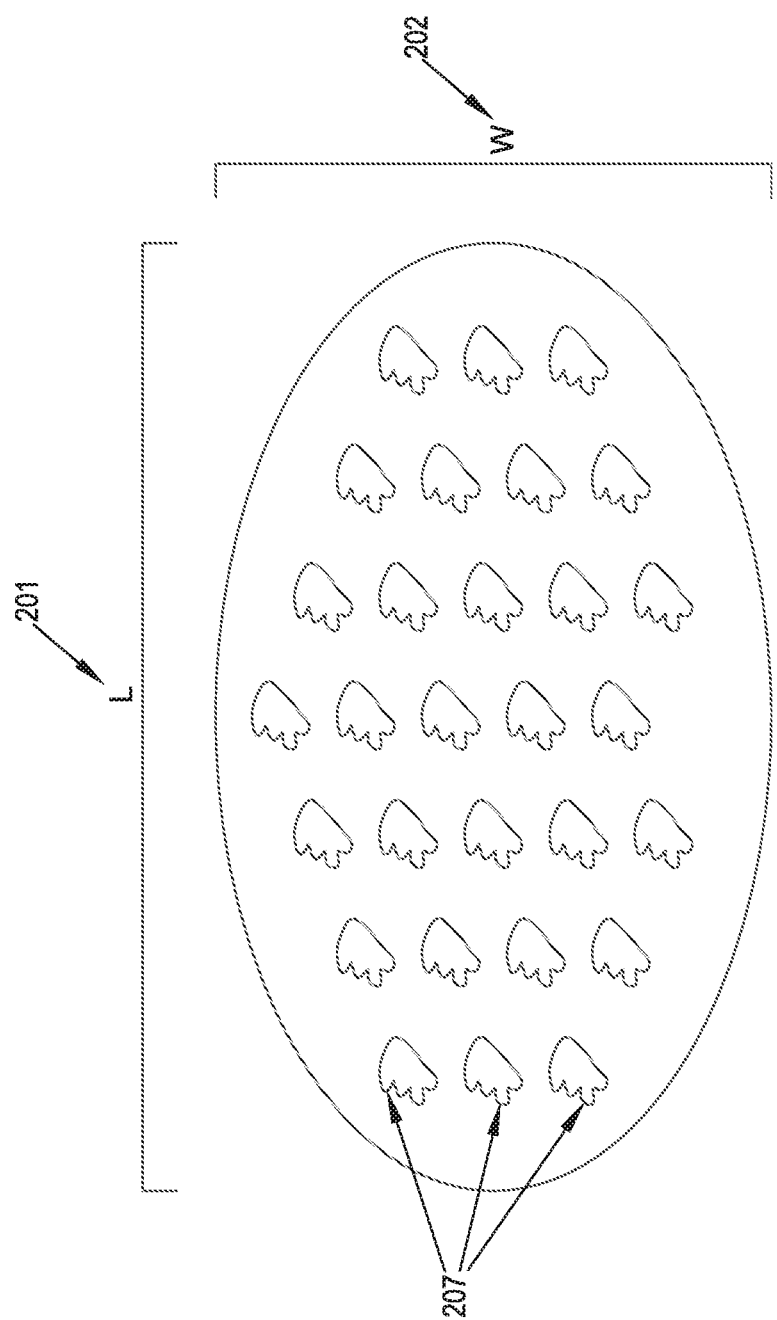

FACIAL SUNSCREEN COMPOSITION

FIELD

The present disclosure relates to non-comedogenic and hypoallergenic sunscreen compositions that comply with COSMOS-standard AISBL.

BACKGROUND

This section provides background information related to the present disclosure which is not necessarily prior art.

Sunscreens are used to protect people from harmful ultraviolet (UV) radiation from the sun that causes sunburn or even skin cancer. However, conventional sunscreens are greasy and whitening when applied, which causes high light reflectivity off of the skin and general uncomfortableness. Additionally, many sunscreens are composed of non-natural components that are either detrimental to the wearer or the environment.

For example, nanoparticles are non-natural components that are added to many sunscreens as UV filters. However, many consider nanoparticles to be toxic to humans because they have been shown to be readily absorbed into the skin, where they can produce DNA-altering free radicals. Other UV filters, such as, for example, oxybenzone, have been shown to mimic hormones when absorbed into the skin. Moreover, many sunscreen components are allergenic and non-comedogenic. Accordingly, sunscreens containing natural components and that are non-greasy and non-whitening are desired.

BRIEF DESCRIPTION OF THE DRAWINGS

The novel features of this disclosure, as well as the disclosure itself, both as to its structure and its operation, will be best understood from the accompanying drawings, taken in conjunction with the accompanying description, in which similar reference characters refer to similar parts and in which:

FIGS. 2B, 2C, 2D and 2E depict top-down views of various embodiments in an oval sheet.

DETAILED DESCRIPTION

Figure 1A:
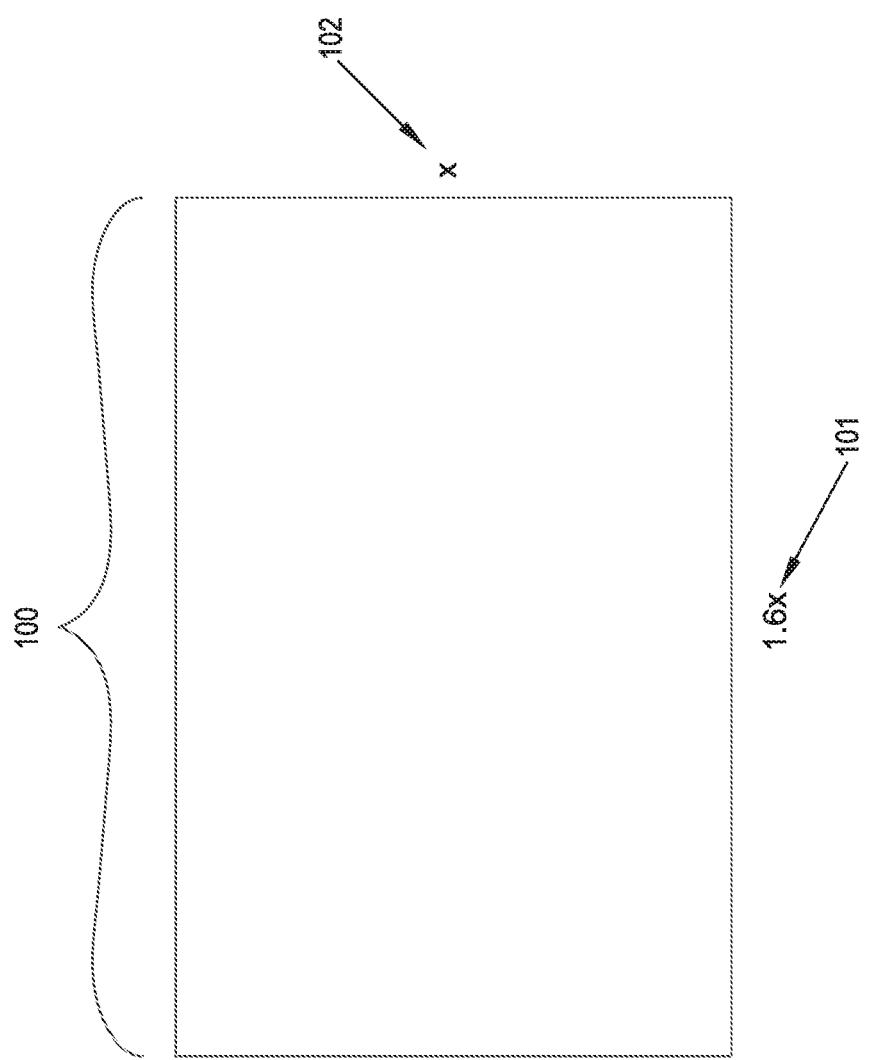
FIG. 1A depicts a top-down view of a rectangular sheet.
Figure 1B:
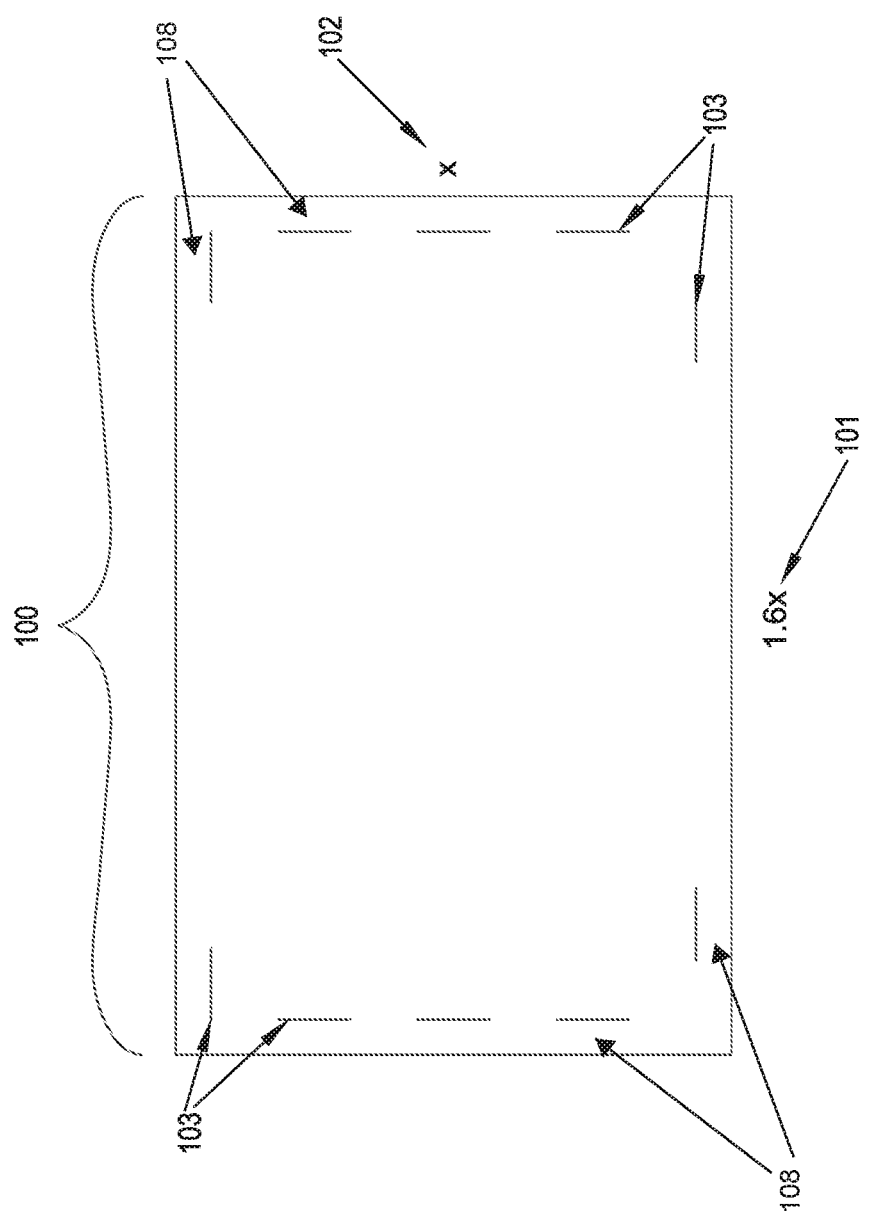
FIGS. 1B, 1C, 1D and 1E depict top-down views of various embodiments in a rectangular sheet.
Figure 1C:
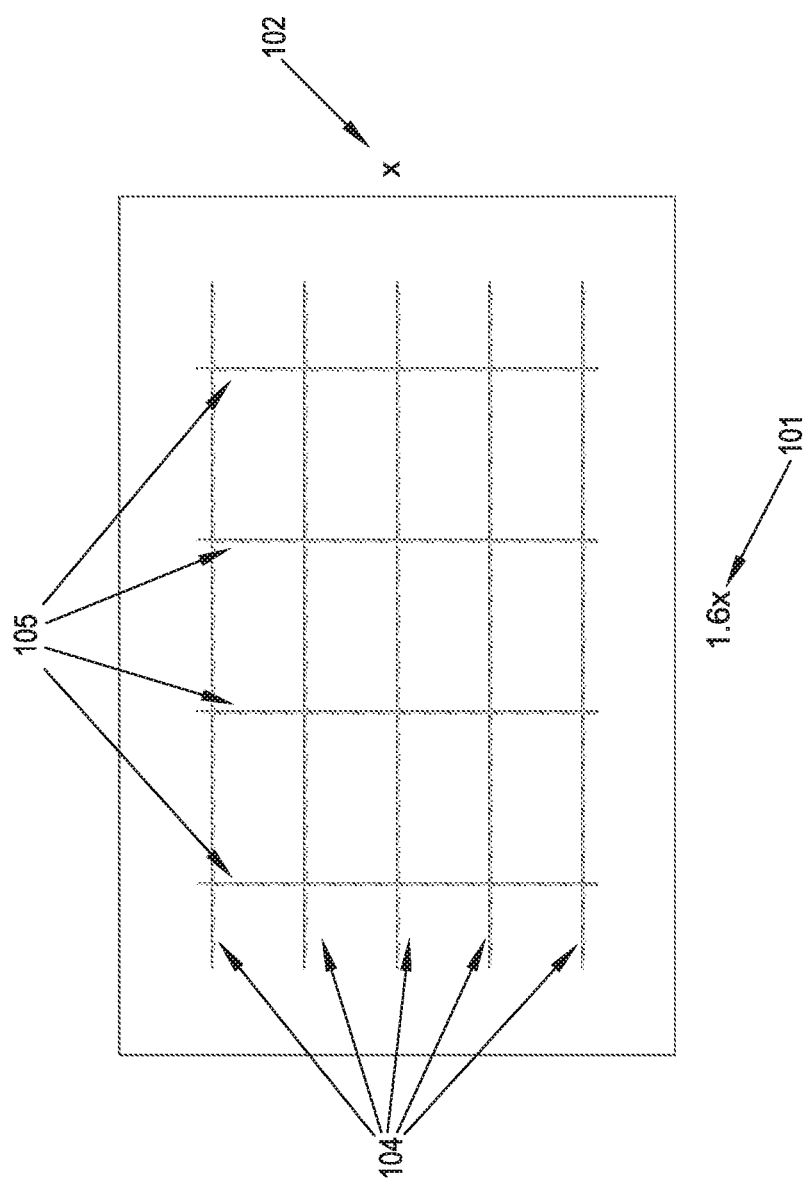
Figure 1D:
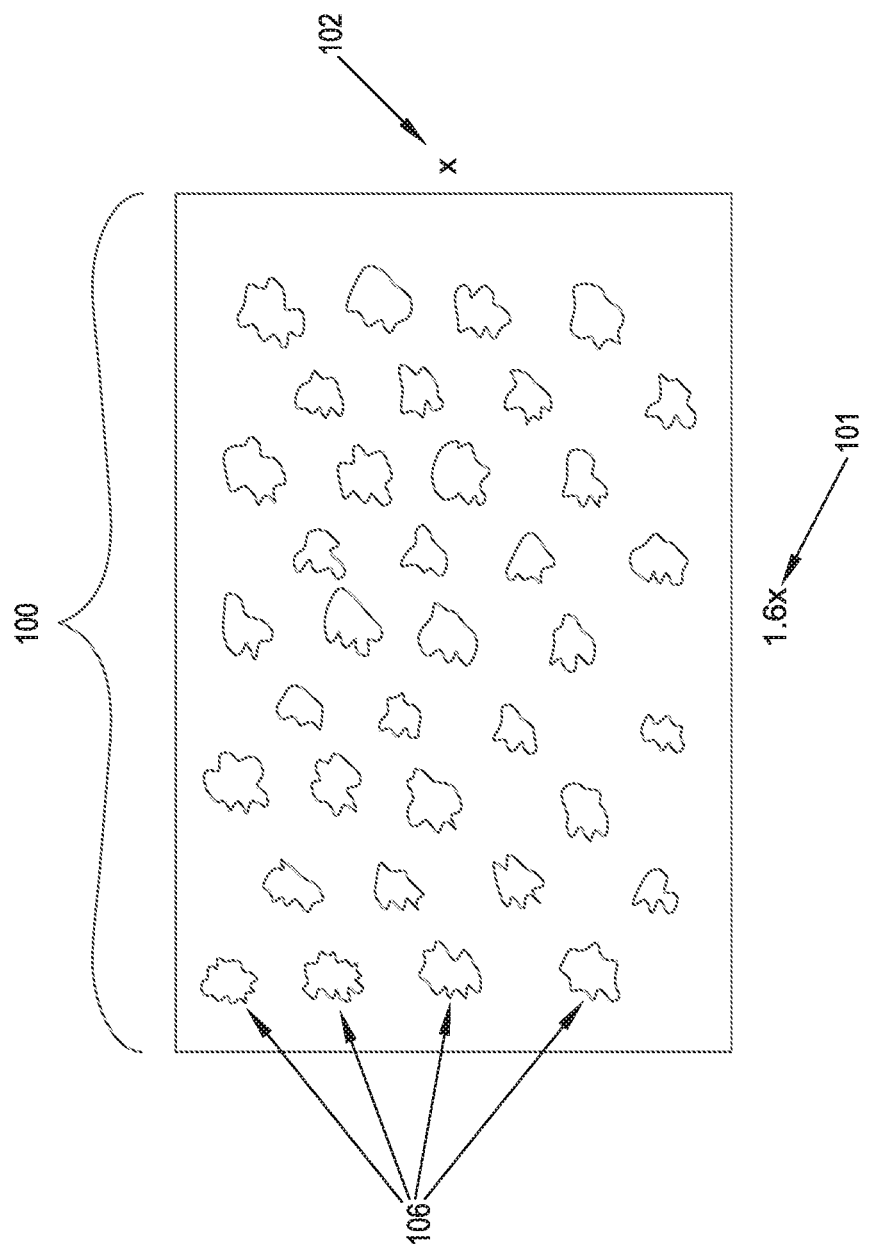

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the stated numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully.

The current technology provides a sunscreen composition that is viscous and non-whitening, non-greasy (i.e., matt finish that yields a low reflectivity), and quick drying. All of the components of the sunscreen composition are natural and comply with the natural product standard governed by Cosmetics Organic and Natural Standard (non-profit) ("COSMOS-standard AISBL"). Accordingly, the sunscreen composition is "COSMOS NATURAL." The current technology also provides wipes that contain the sunscreen composition.

Composition

The sunscreen composition is COSMOS NATURAL. Therefore, each component in the sunscreen composition complies with COSMOS-standard AISBL. The sunscreen composition is also non-comedogenic and hypoallergenic or nonallergenic. As such, each component in the sunscreen composition is non-comedogenic and hypoallergenic or nonallergenic. Therefore, the sunscreen composition will not substantially bock pores or induce substantial allergic reactions. In some embodiments, the sunscreen lotion will not block pores or cause allergic reactions whatsoever.

All of the components of the sunscreen composition are dissolved or suspended in a solvent or carrier. The solvent or carrier is water or an oil.

The active component of the sunscreen provides a sun protection factor (SPF) of greater than or equal to about 5 to less than or equal to about 75, such as an SPF of about 5, about 10, about 15, about 20, about 25, about 30, about 35, about 40, about 45, about 50, about 55, about 60, about 65, about 70, or about 75.

The active component of the sunscreen composition is zinc oxide (ZnO). In all embodiments, regardless of the SPF, the ZnO is present at a concentration of greater than or equal to about 30 wt. % to less than or equal to about 40 wt. %, greater than or equal to about 32 wt. % to less than or equal to about 38 wt. %, or greater than or equal to about 34 wt. % to less than or equal to about 36 wt. %, such as at a concentration of about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, or about 40 wt. %. However, it is understood that the ZnO concentration can be any concentration within the above described ranges, including fractions.

In various embodiments, such as embodiments where the sunscreen composition has an SPF of greater than or equal to about 45, such as an SPF of about 45, about 50, about 55, about 60, about 65, about 70, or about 75, the sunscreen composition further comprises a second active component, wherein the second active component is titanium dioxide ($TiO_2$). The $TiO_2$ is present at a concentration of greater than or equal to about 5 wt. % to less than or equal to about 12 wt. %, greater than or equal to about 6 wt. % to less than or equal to about 11 wt. %, greater than or equal to about 7 wt. % to less than or equal to about 10 wt. %, or greater than or equal to about 8 wt. % to less than or equal to about 9 wt. %, such as at a concentration of about 5 wt. %, about 6 wt. %, about 7 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 10 wt. %, about 11 wt. %, about 12 wt. %. However, it is understood that the $TiO_2$ concentration can be any concentration within the above described ranges, including additional fractions.

As required by COSMOS-standard AISBL, the ZnO and $TiO_2$ are non-nano. For example, COSMOS-standard AISBL defines a "nanomaterial" as an insoluble or biopersistent and intentionally manufactured material with one or more external dimensions, or an internal structure, on the scale from 1 to 100 nm. Therefore, when present, the ZnO and $TiO_2$ are non-nano, i.e., present as particles having a smallest dimension that is greater than 100 nm. The ZnO and $TiO_2$ are substantially free of nanoparticles having a dimension of less than or equal to about 100 nm. By "substantially free" it is meant that of the ZnO and $TiO_2$ particles, they comprise less than about 5%, less than about 2%, or less than about 1% of particles having a dimension of less than or equal to about 100 nm. In some embodiments, the ZnO and $TiO_2$ particles are free of detectable nanoparticles having a dimension of less than or equal to about 100 nm.

In various embodiments, the sunscreen composition further comprises a humectant, i.e., a component that attracts moisture and aids in preventing or inhibiting skin from becoming dry. Non-limiting examples of suitable humectants include glycerin, propylene glycol, diglycerin, sodium pryoglutamic acid (sodium PCA), hyaluroinic acid, pentylene glycol, squalene, sodium hyaluronate, butylene glycol, aloe vera, coconut butter, coconut oil, grape seed oil, *Rubus idaeus* (red raspberry) seed oil, shea butter, and combinations thereof. When included, the humectant is present at a concentration of greater than or equal to about 0.5 wt. % to less than or equal to about 5 wt. %, greater than or equal to about 1 wt. % to less than or equal to about 3 wt. %, or greater than or equal to about 1.5 wt. % to less than or equal to about 2.5 wt. %. In various embodiments, the humectant is present at a concentration of about 0.5 wt. %, about 1 wt. %, about 1.5 wt. %, about 2 wt. %, about 2.5 wt. %, about 3 wt. %, about 3.5 wt. %, about 4 wt. %, about 4.5 wt. %, or about 5 wt. %.

In various embodiments, the sunscreen composition further comprises a thickener, i.e., a component that controls viscosity. Non-limiting examples of suitable thickeners include xanthan gum, cellulose gum, sclerotium gum, pectin, carrageenan, acacia senegal gum, corn starch, ceratonia silique gum, caesalpinia spinose gum, bentonite, microcrystalline cellulose, and combinations thereof. When included, the thickener is present at a concentration of greater than or equal to about 0.01 wt. % to less than or equal to about 0.2 wt. %, or greater than or equal to about 0.05 wt. % to less than or equal to about 0.15 wt. %. In various embodiments, the thickener is present at a concentration of about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, 0.11 wt. %, 0.12 wt. %, 0.13 wt. %, 0.14 wt. %, 0.15 wt. %, 0.16 wt. %, 0.17 wt. %, 0.18 wt. %, 0.19 wt. %, or about 0.2 wt. %.

In various embodiments, the sunscreen composition further comprises a dispersing agent. Non-limiting examples of suitable dispersing agents include polyhydroxystearic acid, isostearic acid, silicone oil, polyglyceryl-3 diisostearate, polyglyceryl-2 dipolyhydroxystearate, and combinations thereof. When included, the dispersing agent is present at a concentration of greater than or equal to about 1 wt. % to less than or equal to about 3 wt. %, or greater than or equal to about 1.5 wt. % to less than or equal to about 2.5 wt. %. In various embodiments, the dispersing agent is present at a concentration of about 1 wt. %, about 1.25 wt. %, about 1.5 wt. %, about 1.75 wt. %, about 2 wt. %, about 2.25 wt. %, about 2.5 wt. %, about 2.75 wt. %, or about 3 wt. %.

In various embodiments, the sunscreen composition further comprises an emulsifier or surfactant. Non-limiting examples of suitable emulsifiers/surfactants include sorbitan monolaurate, glyceryl stearate, polyglyceryl-3 distearate, glyceryl stearate citrate, polyglyceryl-4 oleate, glyceryl oleate, polyglyceryl-4 caprate, polyglyceryl-3 diisostearate, polyglyceryl 3-ricinoleate, polyglyceryl-5 laurate, glyceryl cocoate, glyceryl caprylate, sorbitan tristearate, polyglyceryl-3 pentaolivate, sorbitan olivate, palmitic acid, stearic acid, myristic acid, decyl glucoside, sorbitan oleate, sorbitan stearate, polyglyceryl-10 laurate, polyglyceryl-10 diisostearate, polyglyceryl-2 isostearate, polyglyceryl-6 isostearate, sucrose cocoate, sucrose laurate, sucrose myristate, sucrose palmitate, sucrose stearate, cetearyl glucoside, and combinations thereof. When included, the emulsifier/surfactant is present at a concentration of greater than or equal to about 5 wt. % to less than or equal to about 10 wt. %, greater than or equal to about 5.5 wt. % to less than or equal to about 9.5. wt. %, or greater than or equal to about 6 wt. % to less than or equal to about 9 wt. %. In various embodiments, the emulsifier/surfactant is included at a concentration of about 5 wt. %, about 5.25 wt. %, about 5.5 wt. %, about 5.75 wt. %, about 6 wt. %, about 6.25 wt. %, about 6.5 wt. %, about 6.75 wt. %, about 7 wt. %, about 7.25 wt. %, about 7.5 wt. %, about 7.75 wt. %, about 8 wt. %, about 8.25 wt. %, about 8.5 wt. %, about 8.75 wt. %, about 9 wt. %, about 9.25 wt. %, about 9.5 wt. %, about 9.75 wt. %, or about 10 wt. %. In some embodiments in which the sunscreen composition includes two emulsifiers/surfactants, a first emulsifier/surfactant is included at a concentration of greater than or equal to about 2 wt. % to less than or equal to about 4 wt. % and a second emulsifier/surfactant is included at a concentration of greater than or equal to about 3 wt. % to less than or equal to about 6 wt. %. For example, the first emulsifier/surfactant can have a concentration of about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, or about 4 wt. % and the second emulsifier/surfactant can have a concentration of about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, or about 6 wt. %.

In various embodiments, the sunscreen composition further comprises an emollient, i.e., a component that holds water in skin after application. Non-limiting examples of suitable emollients include cetyl alcohol, butylene glycol, propanediol, cetearyl alcohol, hexyl laurate, myristyl myristate, dicaprylyl ether, caprylic/capric triglyceride, cetyl esters, cetyl palmitate, triisostearine, undecylenic glycerides, lauryl alcohol, decyl oleate, $C_{15-19}$ alkanes, $C_{20-22}$ alcohols, almond oil, candelilla cera, lanolin, hydrogenated vegetable oil, apricot kernel oil, beeswax, avocado oil, babassu oil, sweet almond oil, cocoa butter, jojoba oil, olive oil, hydrogenated castor oil, flax seed oil, jojoba esters, sunflower oil, canola oil, rice germ oil, raspberry oil, and combinations thereof. When included, the emollient is present at a concentration of greater than or equal to about 0.5 wt. % to less than or equal to about 40 wt. %.

However, in various embodiments some of the oils may be present at different concentrations than others. For example, when included, first emollients cetyl alcohol, butylene glycol, propanediol, cetearyl alcohol, hexyl laurate, myristyl myristate, dicaprylyl ether, caprylic/capric triglyceride, cetyl esters, cetyl palmitate, triisostearine, undecylenic glycerides, lauryl alcohol, decyl oleate, $C_{15-19}$ alkanes, $C_{20-22}$ alcohols, and combinations thereof, are individually and independently present at a concentration of greater than or equal to about 0.5 wt. % to less than or equal to about 5 wt. %, greater than or equal to about 0.75 wt. % to less than or equal to about 4 wt. %, or greater than or equal to about 1 wt. % to less than or equal to about 3 wt. %. In various embodiments, the first emollient is present at a concentration of about 0.5 wt. %, about 0.75 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.25 wt. %, about 2.5 wt. %, about 2.75 wt. %, or about 3 wt. %. Further, when included, second emollients almond oil, candelilla cera, lanolin, hydrogenated vegetable oil, apricot kernel oil, beeswax, avocado oil, babassu oil, sweet almond oil, cocoa butter, jojoba oil, olive oil, hydrogenated castor oil, flax seed oil, jojoba esters, sunflower oil, canola oil, rice germ oil, raspberry seed oil, and combinations thereof, are individually and independently present at a concentration of greater than or equal to about 15 wt. % to less than or equal to about 40 wt. %, greater than or equal to about 20 wt. % to less than or equal to about 35 wt. %, or greater than or equal to about 25 wt. % to less than or equal to about 30 wt. %. In various embodiments, the second emollient is present at a concentration of about 15 wt. %, about 20 wt. %, about 25 wt. %, about 30 wt. %, about 35 wt. %, or about 40 wt. %.

In various embodiments, the sunscreen composition further comprises a preservative. Non-limiting examples of suitable preservatives include benzoic acid, benzyl alcohol, sorbic acid, ethyl lactate, sodium benzoate, and combinations thereof. When included, the preservative is present at a concentration of greater than or equal to about 0.1 wt. % to less than or equal to about 2 wt. %, or greater than or equal to about 0.1 wt. % to less than or equal to about 1 wt. %. In various embodiments, the preservative is present at a concentration of about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, or 2 wt. %.

In various embodiments, the sunscreen composition further comprises an antioxidant. Non-limiting examples of suitable antioxidants include tocopherol mixture, ubiquinone, ascorbyl palmitate, triethyl citrate, ferulic acid, and combinations thereof. The tocopherol mixture can be, for example, a mixture of non-α-tocopherol, α-tocopherol, β-tocopherol, γ-tocopherol, and δ-tocopherol. In one embodiment, the tocopherol mixture has a total tocopherol concentration of about 700 mg/g (70%) and includes 560 mg/g (about 56%) non-α-tocopherol, 0-140 (0-14%) mg/g α-tocopherol, 0-70 (0-7%) mg/g β-tocopherol, 350-490 mg/g (35-49%) γ-tocopherol, and 70-210 mg/g (7-21%) δ-tocopherol. Vegetable oils, such as sunflower oil, are suitable sources of tocopherol mixtures. When included, the antioxidant is present at a concentration of greater than or equal to about 0.5 wt. % to less than or equal to about 3 wt. %, greater than or equal to about 1 wt. % to less than or equal to about 2.5 wt. %, or greater than or equal to about 1.5 wt. % to less than or equal to about 2 wt. %. In various embodiments, the antioxidant is present at a concentration of about 0.5 wt. %, about 0.75 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.25 wt. %, about 2.5 wt. %, or about 3 wt. %.

In various embodiments, the sunscreen composition further comprises an odorant, i.e., a component that provides a pleasing scent to the sunscreen composition. Non-limiting examples of suitable odorants include essential oils, such as agar oil, ajwain oil, angelica root oil, anise oil, asafoetida oil, balsam of Peru, basil oil, bay oil, bergamot oil, black pepper oil, buchu oil, birch oil, camphor oil, Ccannabis flower essential oil, calamodin oil, caraway seed oil, Cardamom seed oil, Carrot seed oil, Cedar oil Chamomile oil, Calamus oil, Cinnamon oil, Cistus oil, Citron oil, Citronella oil, Clary Sage oil, Coconut oil, Clove oil, Coffee oil, Coriander oil, Costmary oil, Cranberry seed oil, Cubeb oil, Cypress oil, used in cosmetics, Cypriol oil, Curry leaf oil, Davana oil, from the *Artemisia pallens*, Dill oil, Elecampane oil, Elemi oil, Eucalyptus oil, Fennel seed oil, Fenugreek oil, Fir oil, Frankincense oil, Galangal oil, Galbanum oil, Garlic oil, Geranium oil, Ginger oil, Goldenrod oil, Grapefruit oil, Henna oil, Helichrysum oil, Hickory nut oil, Horseradish oil, Hyssop, Idaho-grown Tansy, Jasmine oil, Juniper berry oil, *Laurus nobilis*, Lavender oil, Ledum, Lemon oil, Lemongrass, Lime, Linalool, Mandarin, Marjoram, Melissa oil (Lemon balm), *Mentha arvensis* oil, Moringa oil, Mountain Savory, Mugwort oil, Mustard oil, Myrrh oil, Myrtle, Neem oil or neem tree oil, Neroli, Nutmeg oil, Orange oil, Oregano oil, Orris oil, Palo Santo, Parsley oil, Patchouli oil, Perilla essential oil, Pennyroyal oil, Peppermint oil, Petitgrain, Pine oil, Ravensara, Red Cedar, Roman Chamomile, Rose oil, Rosehip oil, Rosemary oil, Rosewood oil, Sage oil, Sandalwood oil, Sassafras oil, Savory oil, Schisandra oil, Spearmint oil, Spikenard, Spruce oil, Star anise oil, Tangerine, Tarragon oil, Tea tree oil, Thyme oil, Tsuga, Turmeric, Valerian, Warionia, Vetiver oil (khus oil, Western red cedar, Wintergreen, Yarrow oil, Ylang-ylang, Zedoary, and combinations thereof as non-limiting examples; herbal distillates (also known as floral waters, hydrosols, hydrolates, herbal waters, and essential waters), such as rose water, orange flower water, witch hazel, oregano, thyme, and combinations thereof as non-limiting examples; fruit, such as acai berry, apple, apricot, asian pear, agave, banana, bayberry, bergamot, blueberry, citron, dragon fruit, goji berry, grapefruit, kiwi, lemon, lime, mango, meyer lemon, nectarine, orange, papaya, passion fruit, pear, peach, pineapple, pitanga, plum, pomegranate, ponderosa, quince, raspberry, tangerine, vanilla, vanillin, wintergreen, and combinations thereof as non-limiting examples; floral scent or flower scent, such as volatile organic compounds (VOCs) or aroma compounds emitted by floral tissues, e.g., flower petals; evergreen tropical shrub, such as tiare (Tahitian gardenia or Tiare flower) as a non-limiting example; annuals, such as Evening stock, Flowering tobaccos, Four-o'clock, Fragrant amaryllis, Heliotrope, Mignonette, Night phlox, Peruvian daffodil, Petunia, Stock, Sweet alyssum, Tuberose and Virginian stock, Wallflowers, and combinations thereof as non-limiting examples; perennials, such as Autumn snakeroot, Bouncing Bet, Chocolate daisy, Cut leaf violet, Daffodils and combinations thereof as non-limiting examples; roses, such as Angel Face, Archduke, Buff Beauty, Hansa, Heritage, Louis Philippe, La France, Maggie, Nur Mahal, Pierrine, Souvenir de St. Anne's, Yellow Blaze, and combinations thereof as non-limiting examples; shrubs, such as Azaleas, Banana shrub, Box-leaf azara, Buffalo currant, Carolina allspice or sweetshrub, Daphnes, Fragrant tea olive, Gardenia, Japanese pittosporum, Lilacs, Mexican orange blossom, Mock Sweet box, Sweet pepperbush or summersweet, Viburnums, White forsythia, Winter hazel, Wintersweet, Witch hazels, and combinations thereof as non-limiting examples; vines, such as Variegated kiwi vine, Cinnamon vine, Clematis, Honeysuckle, Jasmines, and combinations thereof as non-limiting examples; trees, such as Amur maple, Black locust, Japanese apricots, Lindens Mt. Etna broom, Yellowwood, and combinations thereof as non-limiting examples; and pods, such as chocolate as a non-limiting example. Any combination of the foregoing odorants can be included in the sunscreen composition as the odorant. When included, individual odorants are present at a concentration of greater than or equal to about 0.01 wt. % to less than or equal to about 2 wt. %, or greater than or equal to about 0.05 wt. % to less than or equal to about 1 wt. %. In various embodiments, the odorant is present at a concentration of about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. %.

In one embodiment, the sunscreen composition has an SPF of greater than or equal to about 5 and less than or equal to about 45 and comprises zinc oxide, a carrier, a humectant, a thickener, a dispersing agent, an emulsifier or surfactant, an emollient, a preservative, and an antioxidant. In another embodiment, the sunscreen composition has an SPF of 30 and consists essentially of zinc oxide, a carrier, a humectant, a thickener, a dispersing agent, an emulsifier or surfactant, an emollient, a preservative, and an antioxidant. In addition to the above definition of "consisting essentially of," the term also means that the composition may include additional small concentrations, i.e., less than or equal to about 10 wt. %, less than or equal to about 5 wt. %, less than or equal to about 2.5 wt. %, or less than or equal to about 1 wt. %, i.e., trace amounts, of at least one component that is not explicitly identified in the sunscreen composition. In yet another embodiment, the sunscreen composition has an SPF of 30 and consists of zinc oxide, a carrier, a humectant, a thickener, a dispersing agent, an emulsifier or surfactant, an emollient, a preservative, and an antioxidant.

In one embodiment, the sunscreen composition has an SPF of greater than or equal to about 5 and less than or equal to about 45 and comprises zinc oxide, water, glycerin, xanthan gum, sorbitan monolaurate, glyceryl stearate, cetyl alcohol, almond oil, benzoic acid, raspberry seed oil, and a tocopherol mixture. In another embodiment, the sunscreen composition has an SPF of 30 and consists essentially of zinc oxide, water, glycerin, xanthan gum, sorbitan monolaurate, glyceryl stearate, cetyl alcohol, almond oil, benzoic acid, raspberry seed oil, and a tocopherol mixture. In yet another embodiment, the sunscreen composition has an SPF of 30 and consists of zinc oxide, water, glycerin, xanthan gum, sorbitan monolaurate, glyceryl stearate, cetyl alcohol, almond oil, benzoic acid, raspberry seed oil, and a tocopherol mixture.

In one embodiment, the sunscreen composition has an SPF of greater than or equal to about 5 and less than or equal to about 45 and comprises zinc oxide, a carrier, a humectant, a thickener, a dispersing agent, an emulsifier or surfactant, an emollient, a preservative, an antioxidant, and an odorant. In another embodiment, the sunscreen composition has an SPF of 30 and consists essentially of zinc oxide, a carrier, a humectant, a thickener, a dispersing agent, an emulsifier or surfactant, an emollient, a preservative, an antioxidant, and an odorant. In yet another embodiment, the sunscreen composition has an SPF of 30 and consists of zinc oxide, a carrier, a humectant, a thickener, a dispersing agent, an emulsifier or surfactant, an emollient, a preservative, an antioxidant, and an odorant.

In one embodiment, the sunscreen composition has an SPF of greater than or equal to about 5 and less than or equal to about 45 and comprises zinc oxide, water, glycerin, xanthan gum, sorbitan monolaurate, glyceryl stearate, cetyl alcohol, almond oil, benzoic acid, raspberry seed oil, a tocopherol mixture, vanillin, and tiare. In another embodiment, the sunscreen composition has an SPF of 30 and consists essentially of zinc oxide, water, glycerin, xanthan gum, sorbitan monolaurate, glyceryl stearate, cetyl alcohol, almond oil, benzoic acid, raspberry seed oil, a tocopherol mixture, vanillin, and tiare. In yet another embodiment, the sunscreen composition has an SPF of 30 and consists of zinc oxide, water, glycerin, xanthan gum, sorbitan monolaurate, glyceryl stearate, cetyl alcohol, almond oil, benzoic acid, raspberry seed oil, a tocopherol mixture, vanillin and tiare.

In one embodiment, the sunscreen composition has an SPF of greater than or equal to about 45 and less than or equal to about 75 and comprises zinc oxide, titanium dioxide, a carrier, a humectant, a thickener, a dispersing agent, an emulsifier or surfactant, an emollient, a preservative, and an antioxidant. In another embodiment, the sunscreen composition has an SPF of 50 and consists essentially of zinc oxide, titanium dioxide, a carrier, a humectant, a thickener, a dispersing agent, an emulsifier or surfactant, an emollient, a preservative, and an antioxidant. In yet another embodiment, the sunscreen composition has an SPF of 50 and consists of zinc oxide, titanium dioxide, a carrier, a humectant, a thickener, a dispersing agent, an emulsifier or surfactant, an emollient, a preservative, and an antioxidant.

In one embodiment, the sunscreen composition has an SPF of greater than or equal to about 45 and less than or equal to about 75 and comprises zinc oxide, titanium dioxide, water, glycerin, polyhydroxystearic acid, glyceryl stearate, sorbitan monolaurate, cetyl alcohol, almond oil, benzoic acid, raspberry seed oil, and a tocopherol mixture. In another embodiment, the sunscreen composition has an SPF of 50 and comprises zinc oxide, titanium dioxide, water, glycerin, polyhydroxystearic acid, glyceryl stearate, sorbitan monolaurate, cetyl alcohol, almond oil, benzoic acid, raspberry seed oil, and a tocopherol mixture. In yet another embodiment, the sunscreen composition has an SPF of 50 and comprises zinc oxide, titanium dioxide, water, glycerin, polyhydroxystearic acid, glyceryl stearate, sorbitan monolaurate, cetyl alcohol, almond oil, benzoic acid, raspberry seed oil, and a tocopherol mixture In one embodiment, the sunscreen composition has an SPF of greater than or equal to about 45 and less than or equal to about 75 and comprises zinc oxide, titanium dioxide, a carrier, a humectant, a thickener, a dispersing agent, an emulsifier or surfactant, an emollient, a preservative, an antioxidant, and an odorant. In another embodiment, the sunscreen composition has an SPF of 50 and consists essentially of zinc oxide, titanium dioxide, a carrier, a humectant, a thickener, a dispersing agent, an emulsifier or surfactant, an emollient, a preservative, an antioxidant, and an odorant. In yet another embodiment, the sunscreen composition has an SPF of 50 and consists of zinc oxide, titanium dioxide, a carrier, a humectant, a thickener, a dispersing agent, an emulsifier or surfactant, an emollient, a preservative, an antioxidant, and an odorant.

In one embodiment, the sunscreen composition has an SPF of greater than or equal to about 45 and less than or equal to about 75 and comprises zinc oxide, titanium dioxide, water, glycerin, polyhydroxystearic acid, glyceryl stearate, sorbitan monolaurate, cetyl alcohol, almond oil, benzoic acid, raspberry seed oil, a tocopherol mixture, vanillin, and tiare. In another embodiment, the sunscreen composition has an SPF of 50 and comprises zinc oxide, titanium dioxide, water, glycerin, polyhydroxystearic acid, glyceryl stearate, sorbitan monolaurate, cetyl alcohol, almond oil, benzoic acid, raspberry seed oil, a tocopherol mixture, vanillin, and tiare. In yet another embodiment, the sunscreen composition has an SPF of 50 and comprises zinc oxide, titanium dioxide, water, glycerin, polyhydroxystearic acid, glyceryl stearate, sorbitan monolaurate, cetyl alcohol, almond oil, benzoic acid, raspberry seed oil, a tocopherol mixture, vanillin, and tiare.

In one embodiment, the sunscreen composition has an SPF of greater than or equal to about 5 and less than or equal to about 45 and comprises non-nano zinc oxide and a carrier, and optionally at least one of a humectant, a thickener, a dispersing agent, an emulsifier or surfactant, an emollient, a preservative, an antioxidant, and an odorant. In another embodiment, the sunscreen composition has an SPF of greater than or equal to about 5 and less than or equal to about 45 and consists essentially of non-nano zinc oxide and a carrier, and at least one of a humectant, a thickener, a dispersing agent, an emulsifier or surfactant, an emollient, a preservative, an antioxidant, and an odorant. In yet another embodiment, the sunscreen composition has an SPF of greater than or equal to about 5 and less than or equal to about 45 and consists of non-nano zinc oxide and a carrier, and at least one of a humectant, a thickener, a dispersing agent, an emulsifier or surfactant, an emollient, a preservative, an antioxidant, and an odorant.

In one embodiment, the sunscreen composition has an SPF of greater than or equal to about 45 and less than or equal to about 75 and comprises non-nano zinc oxide, non-nano titanium dioxide, and a carrier, and optionally at least one of a humectant, a thickener, a dispersing agent, an emulsifier or surfactant, an emollient, a preservative, an antioxidant, and an odorant. In another embodiment, the sunscreen composition has an SPF of greater than or equal to about 45 and less than or equal to about 75 and consists essentially of non-nano zinc oxide, non-nano titanium dioxide, and a carrier, and at least one of a humectant, a thickener, a dispersing agent, an emulsifier or surfactant, an emollient, a preservative, an antioxidant, and an odorant. In yet another embodiment, the sunscreen composition has an SPF of greater than or equal to about 45 and less than or equal to about 75 and consists of non-nano zinc oxide, non-nano titanium dioxide, and a carrier, and at least one of a humectant, a thickener, a dispersing agent, an emulsifier or surfactant, an emollient, a preservative, an antioxidant, and an odorant.

In one embodiment, the sunscreen composition has an SPF of about 30 and comprises greater than or equal to about 34 wt. % to less than or equal to about 36 wt. % non-nano zinc oxide; greater than or equal to about 1.5 wt. % to less than or equal to about 2.5 wt. % glycerine; greater than or equal to about 0.05 wt. % to less than or equal to about 0.15 wt. % xanthan gum; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; and water. In another embodiment, the sunscreen composition has an SPF of about 30 and consists essentially of greater than or equal to about 34 wt. % to less than or equal to about 36 wt. % non-nano zinc oxide; greater than or equal to about 1.5 wt. % to less than or equal to about 2.5 wt. % glycerine; greater than or equal to about 0.05 wt. % to less than or equal to about 0.15 wt. % xanthan gum; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; and water. In yet another embodiment, the sunscreen composition has an SPF of about 30 and consists of greater than or equal to about 34 wt. % to less than or equal to about 36 wt. % non-nano zinc oxide; greater than or equal to about 1.5 wt. % to less than or equal to about 2.5 wt. % glycerine; greater than or equal to about 0.05 wt. % to less than or equal to about 0.15 wt. % xanthan gum; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; and water.

In one embodiment, the sunscreen composition has an SPF of about 30 and comprises greater than or equal to about 34 wt. % to less than or equal to about 36 wt. % non-nano zinc oxide; greater than or equal to about 1.5 wt. % to less than or equal to about 2.5 wt. % glycerine; greater than or equal to about 0.05 wt. % to less than or equal to about 0.15 wt. % xanthan gum; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; greater than or equal to about 0.05 wt. % to less than or equal to about 1 wt. % vanillin; greater than or equal to about 0.05 wt. % to less than or equal to about 1 wt. % tiare; and water. In another embodiment, the sunscreen composition has an SPF of about 30 and consists essentially of greater than or equal to about 34 wt. % to less than or equal to about 36 wt. % non-nano zinc oxide; greater than or equal to about 1.5 wt. % to less than or equal to about 2.5 wt. % glycerine; greater than or equal to about 0.05 wt. % to less than or equal to about 0.15 wt. % xanthan gum; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; greater than or equal to about 0.05 wt. % to less than or equal to about 1 wt. % vanillin; greater than or equal to about 0.05 wt. % to less than or equal to about 1 wt. % tiare; and water. In yet another embodiment, the sunscreen composition has an SPF of about 30 and consists of greater than or equal to about 34 wt. % to less than or equal to about 36 wt. % non-nano zinc oxide; greater than or equal to about 1.5 wt. % to less than or equal to about 2.5 wt. % glycerine; greater than or equal to about 0.05 wt. % to less than or equal to about 0.15 wt. % xanthan gum; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; greater than or equal to about 0.05 wt. % to less than or equal to about 1 wt. % vanillin; greater than or equal to about 0.05 wt. % to less than or equal to about 1 wt. % tiare; and water.

In one embodiment, the sunscreen composition has an SPF of about 50 and comprises greater than or equal to about 34 wt. % to less than or equal to about 36 wt. % non-nano zinc oxide; greater than or equal to about 8 wt. % to less than or equal to about 9 wt. % non-nano titanium dioxide; greater than or equal to about 1.5 wt. % to less than or equal to about 2.5 wt. % glycerine; greater than or equal to about 1.5 wt. % to less than or equal to about 2.5 wt. % polyhydroxystearic acid; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; and water. In another embodiment, the sunscreen composition has an SPF of about 50 and consists essentially of greater than or equal to about 34 wt. % to less than or equal to about 36 wt. % non-nano zinc oxide; greater than or equal to about 8 wt. % to less than or equal to about 9 wt. % non-nano titanium dioxide; greater than or equal to about 1.5 wt. % to less than or equal to about 2.5 wt. % glycerine; greater than or equal to about 1.5 wt. % to less than or equal to about 2.5 wt. % polyhydroxystearic acid; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; and water. In yet another embodiment, the sunscreen composition has an SPF of about 50 and consists of greater than or equal to about 34 wt. % to less than or equal to about 36 wt. % non-nano zinc oxide; greater than or equal to about 8 wt. % to less than or equal to about 9 wt. % non-nano titanium dioxide; greater than or equal to about 1.5 wt. % to less than or equal to about 2.5 wt. % glycerine; greater than or equal to about 1.5 wt. % to less than or equal to about 2.5 wt. % polyhydroxystearic acid; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; and water.

In one embodiment, the sunscreen composition has an SPF of about 50 and comprises greater than or equal to about 34 wt. % to less than or equal to about 36 wt. % non-nano zinc oxide; greater than or equal to about 8 wt. % to less than or equal to about 9 wt. % non-nano titanium dioxide; greater than or equal to about 1.5 wt. % to less than or equal to about 2.5 wt. % glycerine; greater than or equal to about 1.5 wt. % to less than or equal to about 2.5 wt. % polyhydroxystearic acid; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; greater than or equal to about 0.05 wt. % to less than or equal to about 1 wt. % vanillin; greater than or equal to about 0.05 wt. % to less than or equal to about 1 wt. % tiare; and water. In another embodiment, the sunscreen composition has an SPF of about 50 and consists essentially of greater than or equal to about 34 wt. % to less than or equal to about 36 wt. % non-nano zinc oxide; greater than or equal to about 8 wt. % to less than or equal to about 9 wt. % non-nano titanium dioxide; greater than or equal to about 1.5 wt. % to less than or equal to about 2.5 wt. % glycerine; greater than or equal to about 1.5 wt. % to less than or equal to about 2.5 wt. % polyhydroxystearic acid; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; greater than or equal to about 0.05 wt. % to less than or equal to about 1 wt. % vanillin; greater than or equal to about 0.05 wt. % to less than or equal to about 1 wt. % tiare; and water. In yet another embodiment, the sunscreen composition has an SPF of about 50 and consists of greater than or equal to about 34 wt. % to less than or equal to about 36 wt. % non-nano zinc oxide; greater than or equal to about 8 wt. % to less than or equal to about 9 wt. % non-nano titanium dioxide; greater than or equal to about 1.5 wt. % to less than or equal to about 2.5 wt. % glycerine; greater than or equal to about 1.5 wt. % to less than or equal to about 2.5 wt. % polyhydroxystearic acid; greater than or equal to about 2 wt. % to less than or equal to about 4 wt. % sorbitan monolaurate; greater than or equal to about 3 wt. % to less than or equal to about 6 wt. % glyceryl stearate; greater than or equal to about 1 wt. % to less than or equal to about 3 wt. % cetyl alcohol; greater than or equal to about 25 wt. % to less than or equal to about 30 wt. % sunflower oil; greater than or equal to about 0.1 wt. % to less than or equal to about 1 wt. % benzoic acid; greater than or equal to about 1.5 wt. % to less than or equal to about 2 wt. % the tocopherol mixture; greater than or equal to about 0.05 wt. % to less than or equal to about 1 wt. % vanillin; greater than or equal to about 0.05 wt. % to less than or equal to about 1 wt. % tiare; and water.

In one embodiment, the sunscreen composition comprises greater than or equal to about 0.01 wt. % to less than or equal to about 5.00 wt. % xanthan gum; greater than or equal to about 25 wt. % to less than or equal to about 40 wt. % water; greater than or equal to about 10 wt. % to less than or equal to about 25 wt. % sunflower oil; greater than or equal to about 20 wt. % to less than or equal to about 40 wt. % non-nano zinc oxide; greater than or equal to about 1 wt. % to less than or equal to about 10 wt. % sorbitan laurate; greater than or equal to about 1 wt. % to less than or equal to about 10 wt. % glyceryl stearate; greater than or equal to about 0.5 wt. % to less than or equal to about 5 wt. % cetyl alcohol; greater than or equal to about 1 wt. % to less than or equal to about 10 wt. % raspberry seed oil; greater than or equal to about 0.1 wt. % to less than or equal to about 0.5 wt. % benzoic acid; and greater than or equal to about 0.5 wt. % to about 5010.0 wt. % tocopherol.

In some embodiments, the sunscreen composition can include iron oxides, a tinting agent, and/or a coloring agent.

Sunscreen Wipes

The present disclosure is also directed to a sheet that is impregnated with a sunscreen composition. Typically, the exposed surface area of an average adult human's back is approximately 3,114 cm$^2$ and the exposed surface area of an adult human's entire body is approximately 16,300 cm$^2$, requiring about 6.2 grams and about 32.6 grams of sunscreen to meet the SPF requirements, respectively. In some examples, the sheet may be impregnated with between 20,054 milligrams (mg) and 32,510 milligrams (mg) of the sunscreen composition.

The sheet of this disclosure is to be made of a composition which has the following characteristics: insoluble in water, flexible and easily formed into a sheet or towel of many different shapes and sizes, capable of absorbing and retaining the sunscreen composition, unreactive with the components of the sunscreen composition, capable of releasing the sunscreen composition when the user rubs the sheet on their skin and having a high shear and tensile strength.

Insoluble sheets are those which do not dissolve or break apart upon immersion in water. Low viscosity sunscreen compositions formulated to be impregnated into a sheet are often aqueous based. In addition, since the sunscreen may be applied to a wet body, insolubility in water is a desirable feature.

Flexible sheets can be formed from woven or non-woven fibrous materials or a mixture thereof. Non-woven sheets may be preferred for economic reasons. Non-woven sheets are made from individual fibers which are not joined together by a weaving process. Instead, the individual fibers are compacted into a sheet or web structure and bonded together using a chemical, mechanical, or thermal process. The fibers can be randomly oriented or carded into a specific orientation. Although non-woven sheets are preferred for economic reasons, they generally lack the strength of a woven sheet and therefore are susceptible to structural damage such as tearing or ripping.

Woven or non-woven fibrous materials can be either natural or synthetic. Natural fibers are those which are derived from natural sources such as animal, insect or plant. Natural fibers can generally be categorized as being either silk, keratin based, or cellulose based. Synthetic fibers are those which are man-made or originally derived from natural sources and then chemically modified.

Non-limiting examples of keratin based natural fibers useful in the present disclosure are those selected from the group consisting of alpaca hair fibers, camel hair fibers, goat hair fibers, horse hair fibers, wool fibers and other animal hair fibers. Non-limiting examples of cellulose based natural fibers useful in the present disclosure are those selected from the group consisting of cotton fibers, flax fibers, hemp fibers, jute fibers, linen fibers, ramie fibers, sisal fibers and wood pulp.

Non-limiting examples of synthetic fibers useful in the present disclosure are those selected from the group consisting of acetate fibers, acrylic fibers, cellulose ester fibers, modacrylic fibers, polyamide fibers such as nylon fibers and aramid fibers, polyester fibers, polyolefin fibers such as polyethylene fibers and polypropylene fibers, polyethylene terephthalate fibers (PET), polyurethane fibers and foams, polyvinyl chloride fibers and rayon fibers, hydroentangled rayon compositions, spandex fibers, lycra fibers, neoprene fibers, and elastane fibers.

Whether the sheet is woven or non-woven, it can be processed to generate a wide variety of shapes and forms. Non-limiting examples of sheet shapes useful in the present disclosure are those selected from the group consisting of oval, elliptical oval, racetrack oval, rectangle, surfboard, hourglass, egg, triangle, star, square, pentagon, hexagon, heptagon, octagon, heart, diamond, crescent, trapezoid, rhombus, kite, trapezium, marquise, pear, emerald, cushion, baguette, flag, single arrow, double arrow, shamrock, paisley, boat, kidney, demilune, clipped corners square or rectangles, serpentine, cross, moon, butterfly, parallelogram, inverted and tapered hourglass, tapered cylinder, double candlestick, vector shapes, and/or organic shapes.

Sheets may be sized to hold enough sunscreen to cover the entire exposed skin of a variety of body shapes and sizes, including from a small child to a large adult human, or may be sized for only a specific body part such as the back. Although the ranges described herein are for the average adult human, one of ordinary skill in the art will recognize the need to adjust the ranges of sunscreen held by individual sheets based on the changes in body size dictated by, for example, age, weight, height, or body mass.

Sheets may also consist of a single or multiple areas that are not impregnated with a sunscreen composition to allow, for example, for holding the sheet during sunscreen application. To accomplish this, the sheet may have a plastic, resin, film or some other material to separate the impregnated area(s) of the sheet versus the non-impregnated area(s) of the sheet.

Sheets may also include or consist of dyes, paints, tints or emboss to change the color or design of the sheet. Such color or design may be in the form of advertising, decorations, logos, trademarks, company names, images, useful information and the like.

Illustrative and non-limiting examples of three different sheet shapes are depicted in FIGS. 1, 2, and 3. Rectangular sheet 100 in FIG. 1A has elements 101 and 102 showing the length and width dimensions of the sheet, respectively. In an example embodiment, the length/width ratio will be greater than about 1.6. In an example embodiment, the length of the sheet is in the range of about 12 inches to about 100 inches in length and in the range of about 5 inches to about 24 inches in width, more preferably in the range of about 24 inches to about 72 inches in length and in the range of about 6 inches to about 12 inches in width. In addition, the surface area of the sheet designed to absorb and retain the sunscreen formulation will be greater than about 80 square inches. In another embodiment of the present disclosure, each side of the sheet designed to absorb and retain the sunscreen formulation will be greater than about 80 square inches.

Figure 2A:
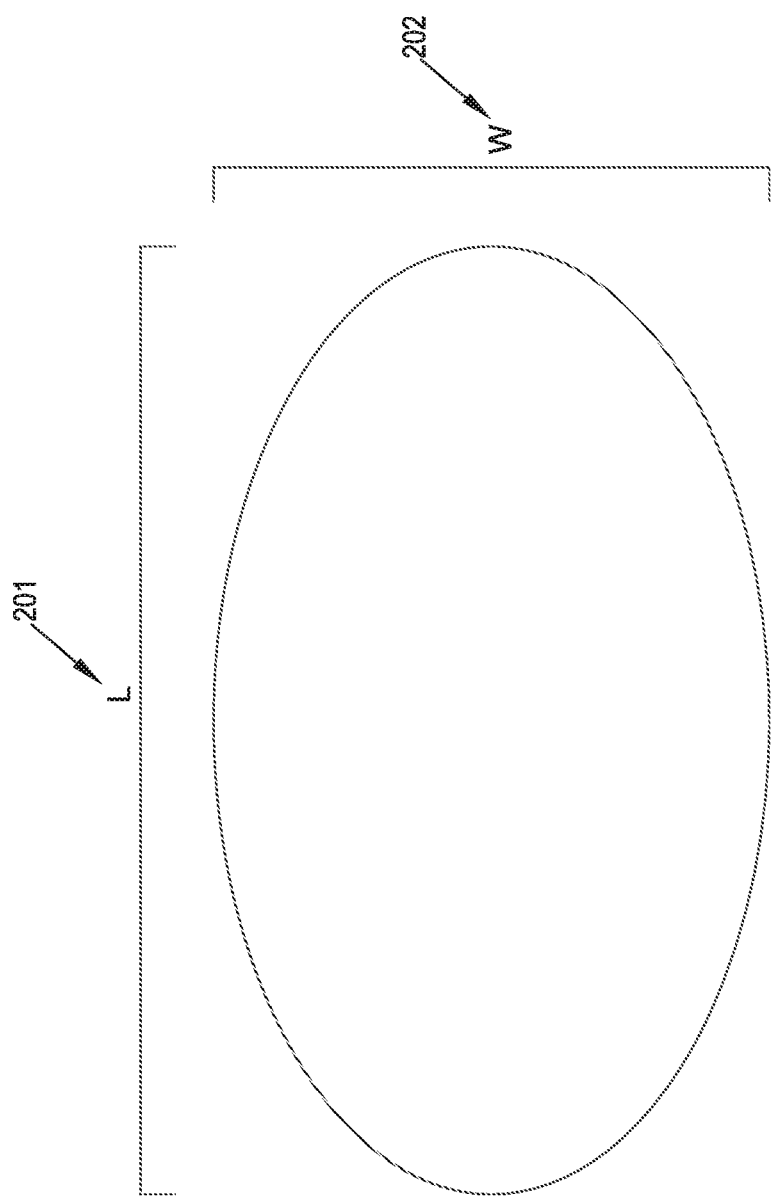
FIG. 2A depicts a top-down view of an oval sheet.
Figure 2B:
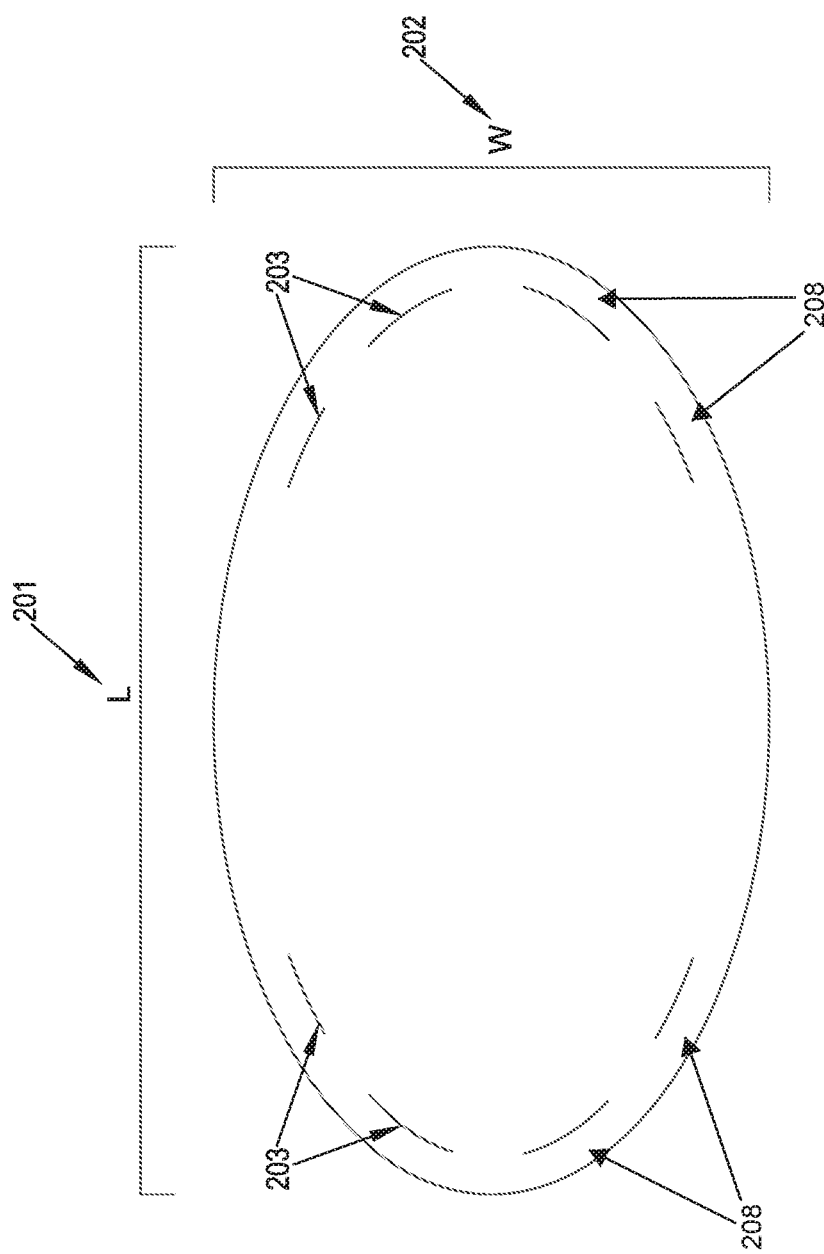
Figure 2C:
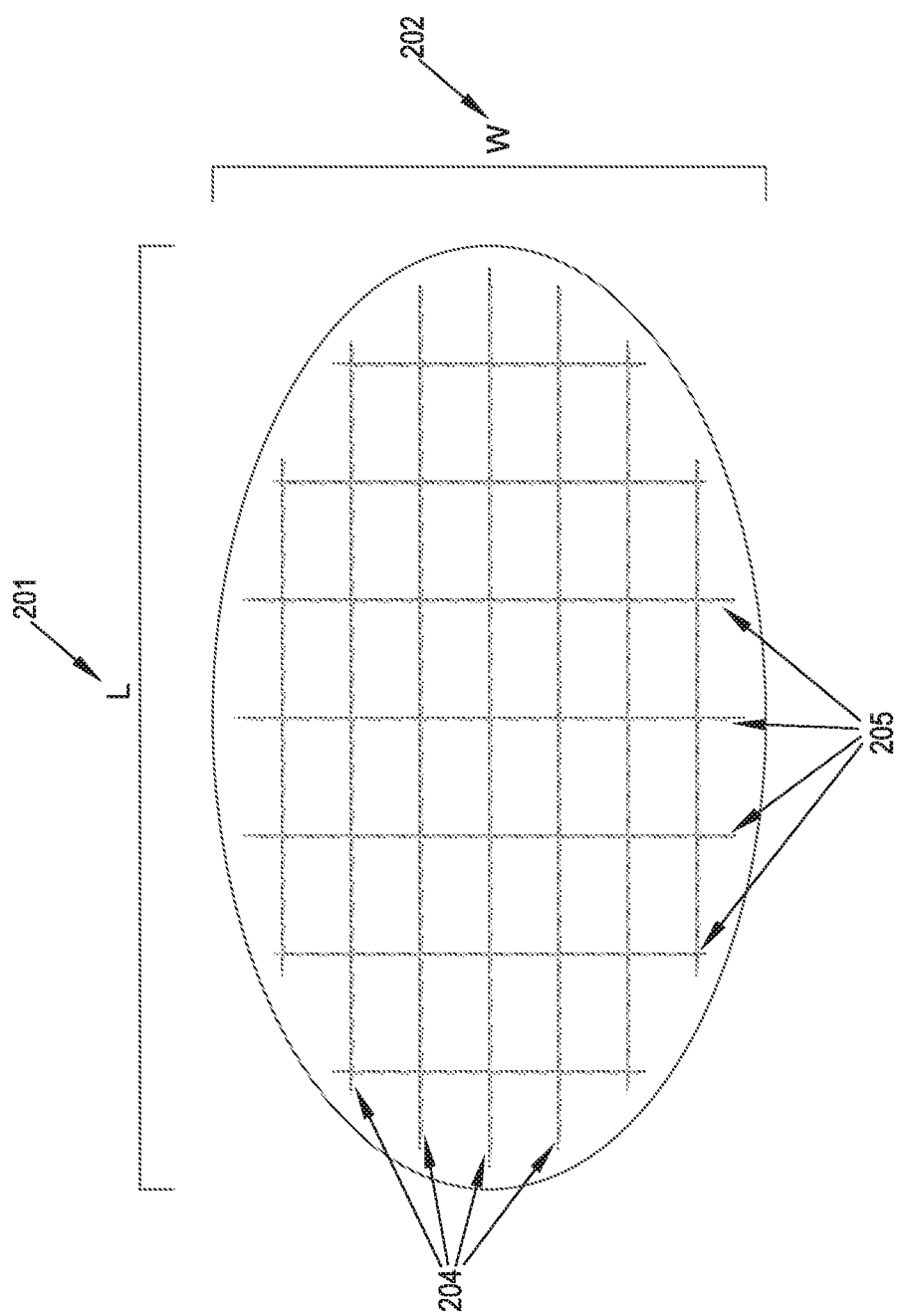
Figure 2D:
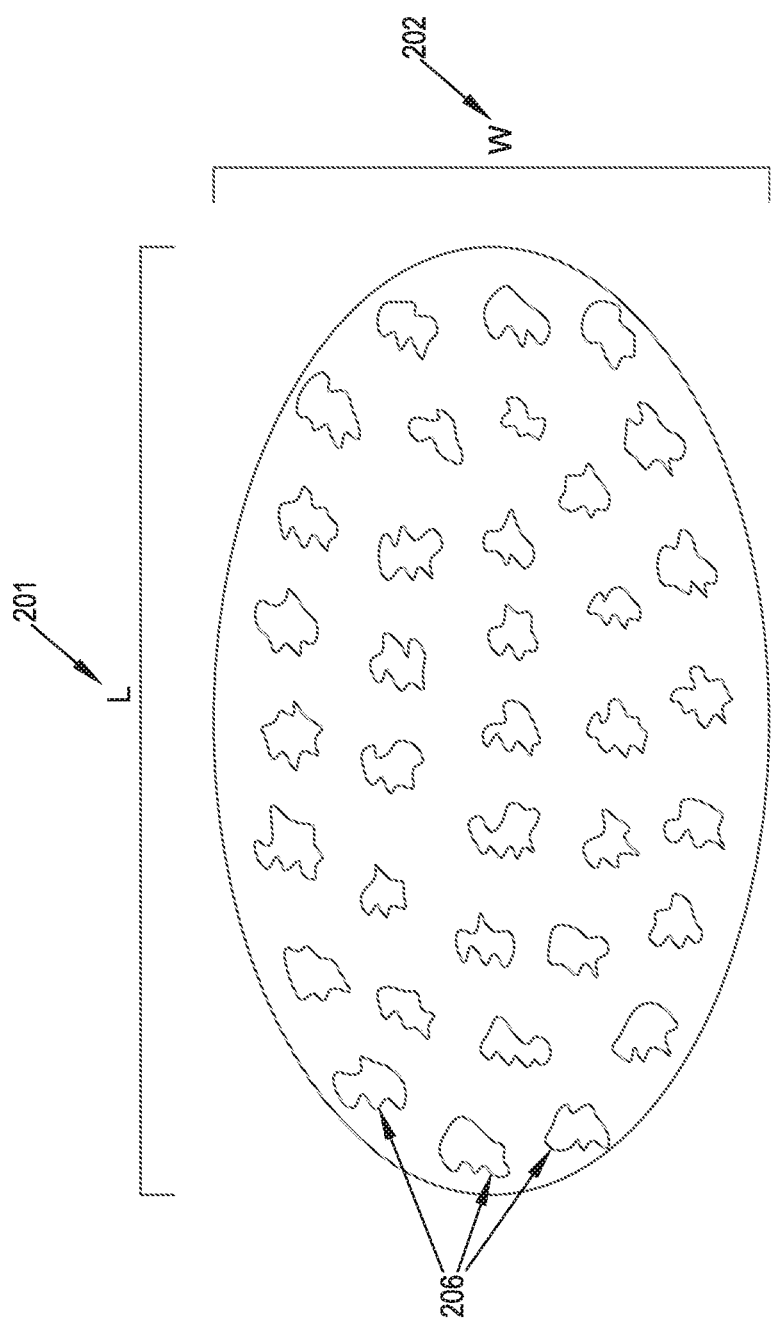

Oval sheet 200 in FIG. 2A has elements 201 and 202 showing the length and width dimensions of the sheet, respectively. Here, width is defined as the largest measurement in the width dimension. In an example embodiment, the length/width ratio will be greater than about 1.6. In an example embodiment, the length of the sheet is in the range of about 12 inches to about 100 inches in length and in the range of about 5 inches to about 24 inches in width, more preferably in the range of about 24 inches to about 72 inches in length and in the range of about 6 inches to about 12 inches in width. In addition, the surface area of the sheet designed to absorb and retain the sunscreen formulation will be greater than about 80 square inches. In another embodiment, the surface area of each side of the sheet designed to absorb and retain the sunscreen formulation will be greater than about 80 square inches.

Figure 3A:
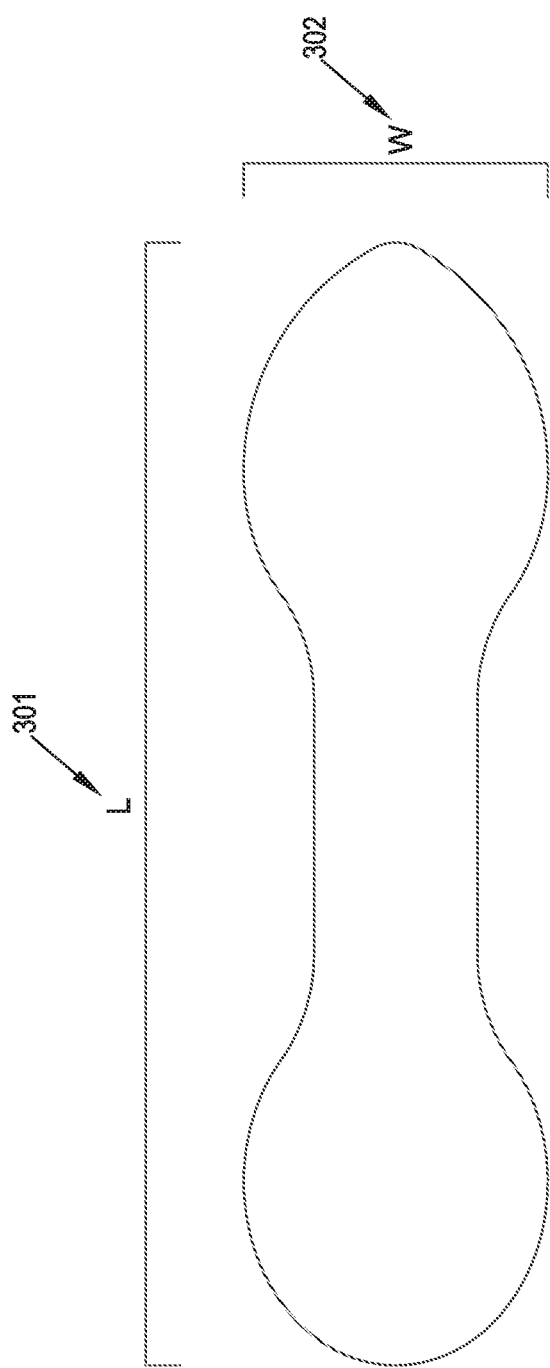
FIG. 3A depicts a top-down view of an hourglass sheet.
Figure 3B:
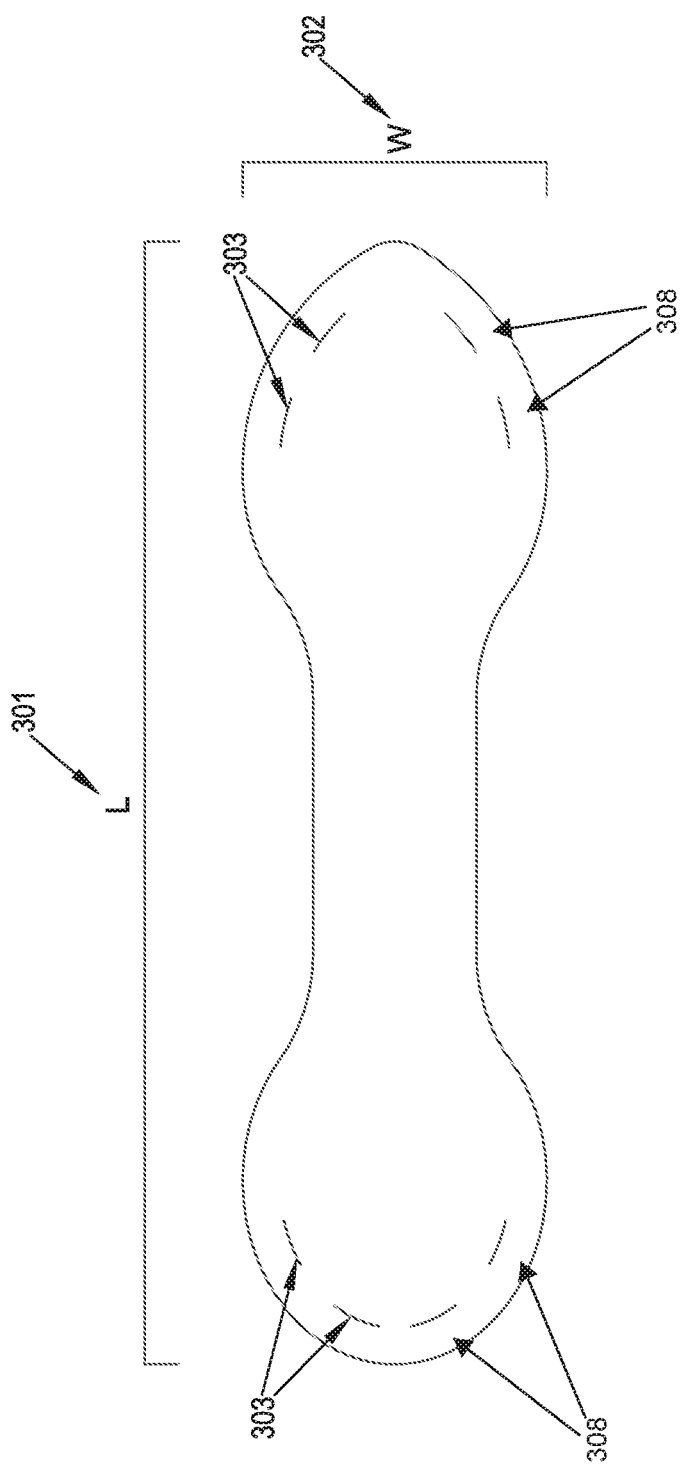
FIGS. 3B, 3C, 3D and 3E depict top-down views of various embodiments in an hourglass sheet.
Figure 3C:
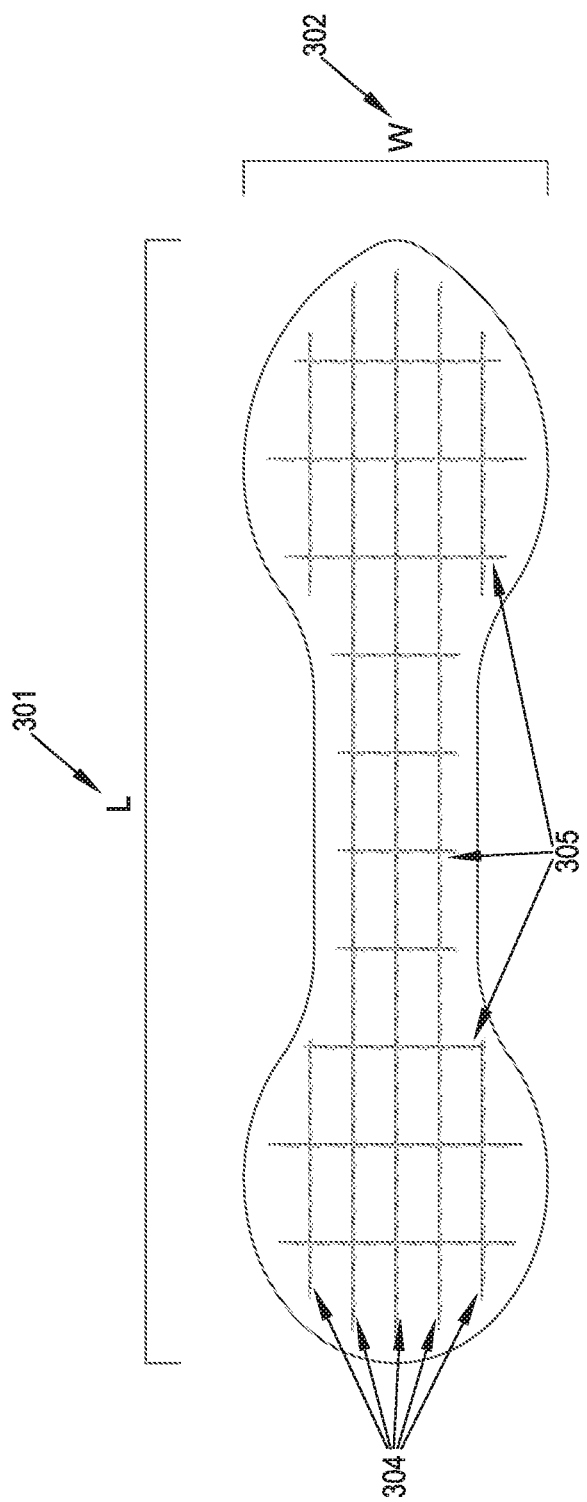
Figure 3D:
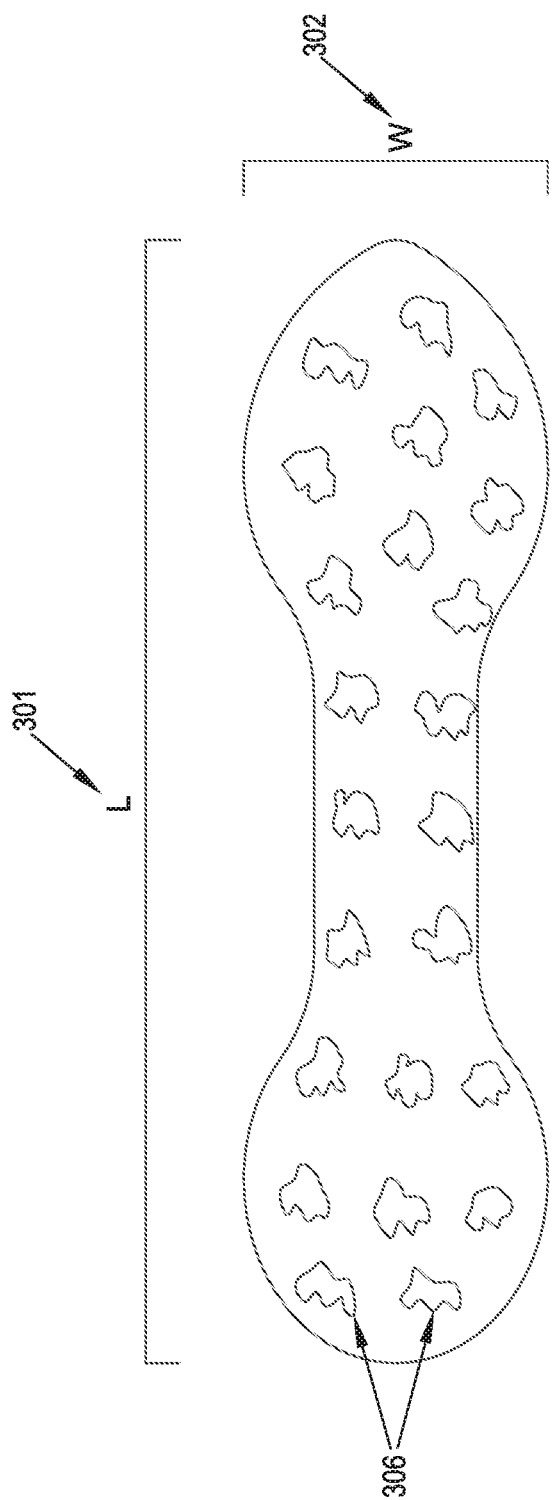

Hourglass sheet 300 in FIG. 3A has elements 301 and 302 showing the length and width dimensions of the sheet, respectively. Here, width is defined as the largest measurement in the width dimension. In an example embodiment, the length/width ratio will be greater than about 1.6. In an example embodiment, the length of the sheet is in the range of about 12 inches to about 100 inches in length and in the range of about 5 inches to about 24 inches in width, more preferably in the range of about 24 inches to about 72 inches in length and in the range of about 6 inches to about 12 inches in width. In addition, the surface area of the sheet designed to absorb and retain the sunscreen formulation will be greater than about 80 square inches. In another embodiment, the surface area of each side of the sheet designed to absorb and retain the sunscreen formulation will be greater than about 80 square inches.

In a specific embodiment of the present disclosure, a user may utilize the impregnated sheet to apply sunscreen to the user's back or entire exposed skin with or without assistance from another person. Consequently, structural modifications such as the addition of hand slits, mitts or finger holes incorporated into the perimeter of the sheet, which enable the user to grasp the sheet, are contemplated. Mitts 103, 203, and 303 are depicted in FIGS. 1B, 2B, 3B, and 3F, respectively. Structural modifications may also include or consist of a single or multiple areas that are not impregnated with a sunscreen composition to allow, for example, for holding the sheet during sunscreen application. Non-impregnated area 108, 208, and 308 are depicted in FIGS. 1B, 2B, 3B, and 3F, respectively. The non-impregnated area may have a plastic, resin, film, or some other material to separate the impregnated area(s) of the sheet versus the non-impregnated area(s) of the sheet.

Woven and non-woven sheets impregnated with a sunscreen composition are often subject to tearing due to the decreased wet strength. Consequently, it is desirable to increase the mechanical strength of the sheet to prevent ripping or tearing during application. The sheet can incorporate structural modifications in order to increase the mechanical strength properties. Non-limiting examples of structural modifications intended to increase the mechanical strength of the sheet useful in the present disclosure are those selected from the group consisting of horizontal stitching, vertical stitching, adhering the sheet to a plastic or rubber structural backing, and adhering a plastic or rubber structural backing between two sheet layers. Horizontal stitching 104, 204, and 304 as well as vertical stitching 105, 205, and 305 are depicted in FIGS. 1C, 2C, 3C and 3F, respectively. Adhering a sheet to a structural backing is depicted in FIG. 4A, while adhering a structural backing to and between two sheets is depicted in FIG. 4B.

In addition to these structural modifications, other modifications such as adding thermal or chemical binders, including, but not limited to plastics, rubbers, or resins can be incorporated into the fabric to increase the mechanical strength of the sheet.

Figure 1E:
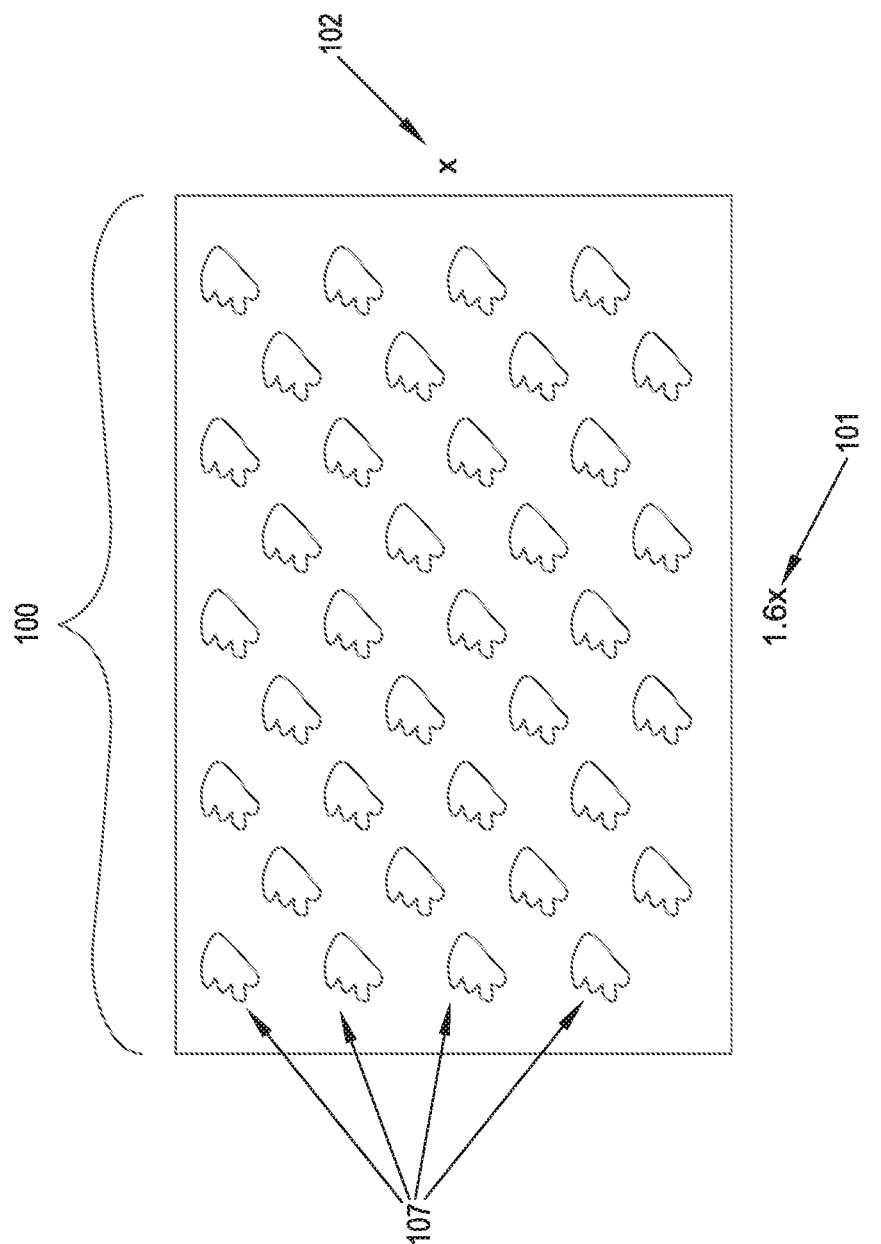
Figure 3E:
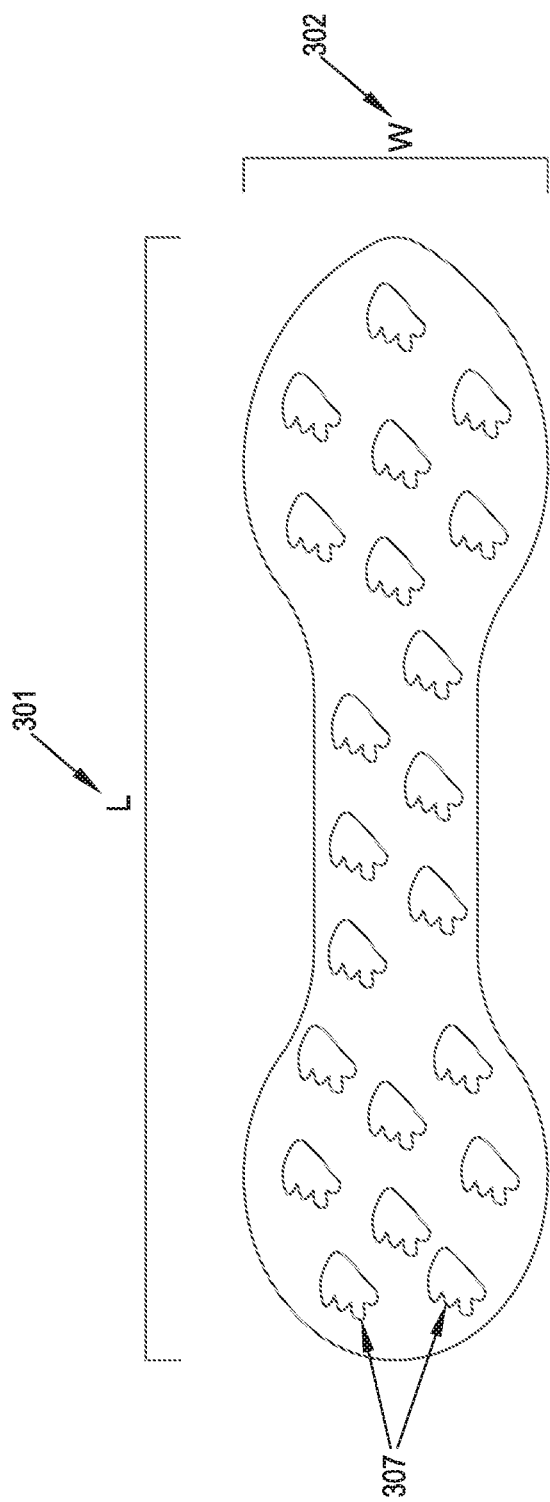

One aspect of the disclosure is to create a sheet which can retain enough sunscreen composition to apply an even coating to an adult or other human's back or entire body, at least one time. Therefore, the addition of quilting or a granulated/textured surface to the sheet is contemplated. FIGS. 1D, 2D, 3D, and 3F depict irregular quilting 106, 206, and 306, respectively, added to the surface of the sheet. FIGS. 1E, 2E, and 3E depict regular quilting 107, 207, and 307, respectively added to the surface of the sheet.

Figure 3F:
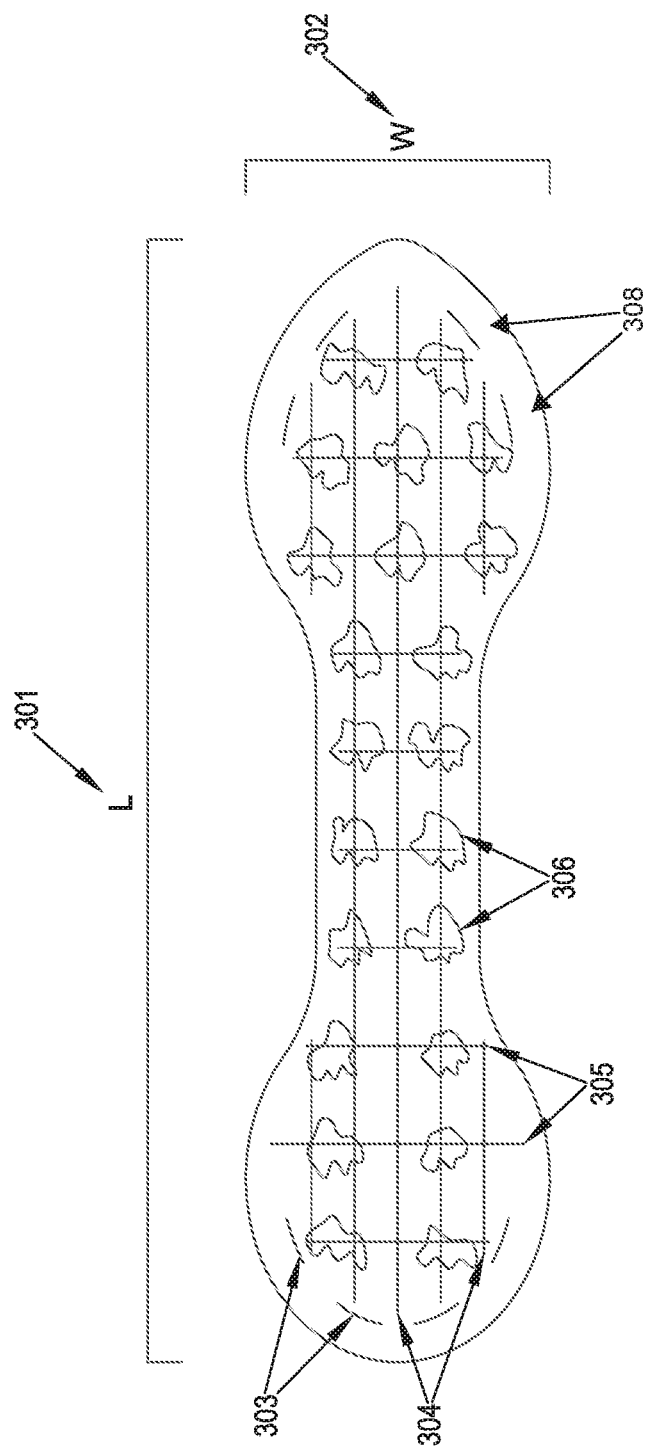
FIG. 3F depicts a top-down view of all the embodiments depicted in FIGS. 3B, 3C and 3D.
Figure 4A:
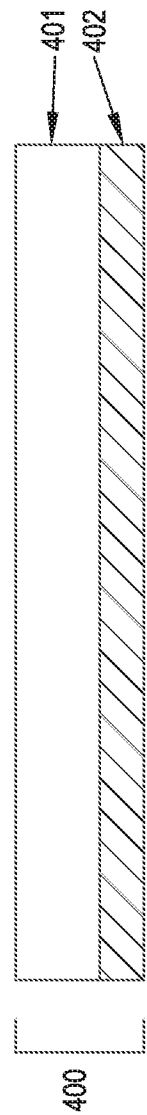
FIG. 4A depicts a sheet adhered to a structural backing.
Figure 4B:
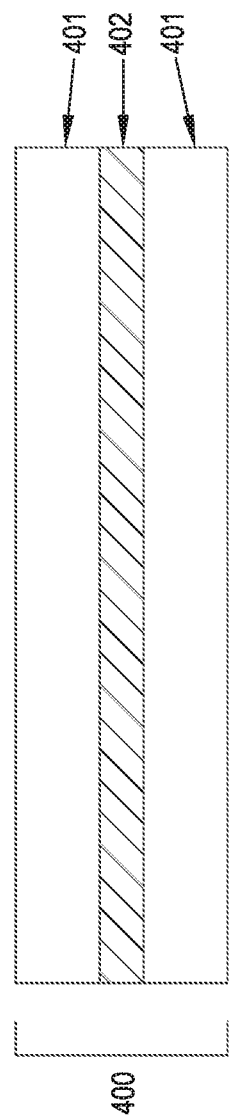
FIG. 4B depicts a structural backing adhered to and sandwiched between two sheets.

As an illustrative and non-limiting example of the present disclosure, mitts 303, horizontal stitching 304, vertical stitching 305, and irregular quilting 306 are depicted on an hourglass sheet in FIG. 3F. It should be apparent to one of ordinary skill in the art that any combination of these embodiments and others can be employed on any shaped sheet. It should also be apparent to one of ordinary skill in the art that any combination of these embodiments and others can be applied to sheets adhered to structural backing The sunscreen composition will be formulated to be sufficiently fluid to allow absorption and retention in the sheet. Non-limiting formulations useful in the present disclosure may be selected from the group consisting of oils, gels, creams, lotions, liquids, and others. Furthermore, the composition will be released from the sheet upon gentle rubbing over the user's skin and will, preferably, form a thin, non-greasy, and non-tacky film over the user's skin.

UV blocking agents are well known in the art. Broad-spectrum sunscreens are able to block both UV-A and UV-B radiation, corresponding to wavelengths between about 280 nm to about 400 nm. It is also well known that UV blacking agents are made of either organic molecules, which absorb UV radiation or inorganic particles, which reflect or scatter UV radiation. Additionally, there is a newer class of organic molecule particulates which both absorb and scatter UV radiation. Non-limiting agents useful in the present disclosure will be selected from the group consisting of amiloxate, avobenzone, bemotrizinol, bisoctrizole, cinoxate, dioxybenzone, drometrizole trisiloxane, ecamsule, enzacamene, homosalate, iscotrizinol, menthyl anthranilate, octinoxate, octocrylene, octyl methoxycinnamate, octyl salicylate, octyl triazone, oxybenzone, padimate O, para-aminobenzoic acid, phenylbenzimidazole sulfonic acid, sulisobenzone, trolamine salicylate, titanium dioxide, and zinc oxide or other UB blocking agents.

Additional UV blocking agents useful in the present disclosure may be selected from the group consisting of benzophenone-9, 4-methylbenzylidene camphor, isopentenyl-4-methoxycinnamate, Mexoryl XL, Neo Heliopan AP, Parsol SLX, Tinosorb M, Tinosorb S, Uvasorb HEB, Uvinul A Plus and Uvinul T 150 or other UV blocking agents.

In order to reduce the viscosity of the sunscreen formulation, a solvent system often consisting of water and/or alcohol is often used. If the alcohol content is too high, the sunscreen may cause an unwanted burning sensation and/or drying of the user's skin. If the water content is too high, emulsification of the hydrophobic blocking agents is often difficult to achieve. Thus, the sunscreen formulation will be balanced such that the viscosity is low enough to allow uptake and absorption of the formulation into the sheet while the hydrophobic blocking agents are emulsified and distributed in the solvent system.

Due to the fact that the blocking agents are often hydrophobic and insoluble in water, a surfactant or emulsifier system is also incorporated into the formulation to disperse the blocking agents in the solvent system. Non-limiting surfactants or emulsifiers useful in the present disclosure can be selected from the group consisting of anionic surfactants, cationic surfactants, nonionic surfactants, amphoteric surfactants, and others.

In addition, emollients and other inactive compounds are often used in sunscreen formulations to moisten the user's skin and provide other benefits. Non-limiting inactive compounds useful in the present disclosure can be selected from the group consisting of hydrocarbons, silicones, fatty alcohols, synthetic esters, natural esters, Vitamin A, Vitamin B, and Vitamin C, as well as herbal and botanical extracts.

It should be recognized by one of ordinary skill in the art that the sheets described herein may be used to apply other compositions besides sunscreen. Non-limiting examples of other compositions capable of being applied with a sheet set forth in this description can be selected from the group consisting of moisturizing compositions, anti-aging compositions, insect repellent compositions, anti-bacterial compositions, anti-inflammatory compositions, anti-fungal compositions, sun burn treatment compositions, makeup compositions, dermatological compositions, pharmaceutical compositions, medical compositions, and others.

The sheets 100, 200, 300 may comprise properties to withstand breakdown due to impregnation of the sunscreen composition. For example, a water-insoluble non-woven sheet (e.g., sheets 100, 200, 300) may have a length to width ratio of greater than about 1.6 to 1 and a tensile strength ranging between 15.5 lbs. and 29 lbs., perpendicular to a grain of the water-insoluble non-woven sheet. The water-insoluble non-woven sheet may also comprise a basis weight ranging between 1.6 ounces per square yard and 1.7 ounces per square yard. The water-insoluble non-woven sheet may also comprise a thickness ranging between 9 mils and 11 mils.

In one or more embodiments of the present disclosure, between 20 g and 33 g of the sunscreen composition is required to cover an average body. Therefore, the wipe described above should contain greater than or equal to about 10 g, greater than or equal to about 33 g, greater than or equal to about 35 g, or greater than or equal to about 40 g of the sunscreen composition. In various embodiments the wipe contains about 10 g, about 11 g, about 12 g, about 13 g, about 14 g, about 15 g, about 16 g, about 17 g, about 18 g, about 19 g, about 20 g, about 21 g, about 22 g, about 23 g, about 24 g, about 25 g, about 26 g, about 27 g, about 28 g, about 29 g, about 30 g, about 31 g, about 32 g, about 33 g, about 34 g, about 35 g, about 36 g, about 37 g, about 38 g, about 39 g, about 40 g, about 41 g, about 42 g, about 43 g, about 44 g, about 45 g, about 46 g, about 47 g, about 48 g about 49 g, about 50 g, about 51 g, about 52 g, about 53 g, about 54 g, about 55 g, about 56 g, about 57 g, about 58 g, about 59 g, or about 60 g of the sunscreen composition.

The sheets 100, 200, 300 may comprise various physical properties to accommodate users. For example, the sheets 100, 200, 300 may have a surface that may be cool, slick, smooth, loose, stiff, heavy, and/or stretch. The sheets 100, 200, 300 may have a texture that may be smooth or textured. The sheets 100, 200, 300, may also include apertures. In various implementations, the sheets 100, 200, 300, may include a randomized pattern of apertures or may include a structured pattern of apertures, or combinations thereof.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A sunscreen composition comprising:
greater than or equal to about 34 wt. % to less than or equal to about 36 wt. % non-nano zinc oxide;
greater than or equal to about 1.5 wt. % to less than or equal to about 2.5 wt. % glycerine;
greater than or equal to about 3 wt. % to less than or equal to about 6 wt. % glyceryl stearate;
greater than or equal to about 25 wt. % to less than or equal to about 30 wt. % sunflower oil;
greater than or equal to about 0.1 wt. % to less than or equal to about 1 wt. % benzoic acid; and
greater than or equal to about 0.5 wt. % to less than or equal to about 3 wt. % a tocopherol mixture.

2. The sunscreen composition as recited in claim 1, further comprising: greater than or equal to about 2 wt. % to less than or equal to about 4 wt. % sorbitan monolaurate.

3. The sunscreen composition as recited in claim 2, further comprising: greater than or equal to about 1 wt. % to less than or equal to about 3 wt. % cetyl alcohol.

4. The sunscreen composition as recited in claim 3, further comprising: greater than or equal to about 0.05 wt. % to less than or equal to about 0.15 wt. % xanthan gum.

5. The sunscreen composition as recited in claim 2, further comprising: greater than or equal to about 8 wt. % to less than or equal to about 9 wt. % non-nano titanium dioxide.

6. The sunscreen composition as recited in claim 5, further comprising: greater than or equal to about 1.5 wt. % to less than or equal to about 2.5 wt. % polyhydroxystearic acid.

7. The sunscreen composition as recited in claim 1, wherein the tocopherol mixture comprises an amount greater than or equal to about 1 wt. % to less than or equal to about 2.5 wt. %.

8. A sunscreen composition comprising:
greater than or equal to about 34 wt. % to less than or equal to about 36 wt. % non-nano zinc oxide;
greater than or equal to about 0.5 wt. % to less than or equal to about 5 wt. % glycerine;
greater than or equal to about 3 wt. % to less than or equal to about 6 wt. % glyceryl stearate;
greater than or equal to about 25 wt. % to less than or equal to about 30 wt. % sunflower oil;
greater than or equal to about 0.1 wt. % to less than or equal to about 1 wt. % benzoic acid; and
greater than or equal to about 0.5 wt. % to less than or equal to about 3 wt. % a tocopherol mixture.

9. The sunscreen composition as recited in claim 8, further comprising: greater than or equal to about 2 wt. % to less than or equal to about 4 wt. % sorbitan monolaurate.

10. The sunscreen composition as recited in claim 9, further comprising: greater than or equal to about 1 wt. % to less than or equal to about 3 wt. % cetyl alcohol.

11. The sunscreen composition as recited in claim 10, further comprising: greater than or equal to about 0.05 wt. % to less than or equal to about 0.15 wt. % xanthan gum.

12. The sunscreen composition as recited in claim 10, further comprising: greater than or equal to about 8 wt. % to less than or equal to about 9 wt. % non-nano titanium dioxide.

13. The sunscreen composition as recited in claim 12, further comprising: greater than or equal to about 1.5 wt. % to less than or equal to about 2.5 wt. % polyhydroxystearic acid.

14. The sunscreen composition as recited in claim 8, wherein the tocopherol mixture comprises an amount greater than or equal to about 1 wt. % to less than or equal to about 2.5 wt. %.

15. A sunscreen composition comprising:
greater than or equal to about 34 wt. % to less than or equal to about 36 wt. % non-nano zinc oxide;
greater than or equal to about 0.5 wt. % to less than or equal to about 5 wt. % glycerine;
greater than or equal to about 3 wt. % to less than or equal to about 6 wt. % glyceryl stearate;
greater than or equal to about 25 wt. % to less than or equal to about 30 wt. % sunflower oil;
greater than or equal to about 0.1 wt. % to less than or equal to about 1 wt. % benzoic acid; and greater than or equal to about 1 wt. % to less than or equal to about 2.5 wt. % a tocopherol mixture.

16. The sunscreen composition as recited in claim 8, further comprising: greater than or equal to about 2 wt. % to less than or equal to about 4 wt. % sorbitan monolaurate.

17. The sunscreen composition as recited in claim 9, further comprising: greater than or equal to about 1 wt. % to less than or equal to about 3 wt. % cetyl alcohol.

18. The sunscreen composition as recited in claim 10, further comprising: greater than or equal to about 0.05 wt. % to less than or equal to about 0.15 wt. % xanthan gum.

19. The sunscreen composition as recited in claim 10, further comprising: greater than or equal to about 8 wt. % to less than or equal to about 9 wt. % non-nano titanium dioxide.

20. The sunscreen composition as recited in claim 12, further comprising: greater than or equal to about 1.5 wt. % to less than or equal to about 2.5 wt. % polyhydroxystearic acid.

* * * * *